(12) United States Patent
Sand

(10) Patent No.: US 7,044,945 B2
(45) Date of Patent: May 16, 2006

(54) PREVENTION OF REGRESSION IN THERMAL CILIARY MUSCLE TENDINOPLASTY

(76) Inventor: Bruce J. Sand, 3957 Cresthaven Dr., Westlake Village, CA (US) 91362

( * ) Notice: Subject to any disclaimer, the term of this patent is extended or adjusted under 35 U.S.C. 154(b) by 292 days.

(21) Appl. No.: 10/400,173

(22) Filed: Mar. 26, 2003

(65) Prior Publication Data

US 2004/0093046 A1 May 13, 2004

Related U.S. Application Data

(63) Continuation-in-part of application No. 10/229,762, filed on Aug. 28, 2002, which is a continuation-in-part of application No. 10/113,361, filed on Mar. 29, 2002, now abandoned.

(60) Provisional application No. 60/280,670, filed on Mar. 30, 2001, provisional application No. 60/311,518, filed on Aug. 11, 2001.

(51) Int. Cl.
    *A61B 18/04* (2006.01)

(52) U.S. Cl. .............. 606/12; 606/13; 606/31; 606/42; 607/88; 607/102; 607/104; 128/898

(58) Field of Classification Search ............ 606/5, 606/10, 13, 27–31, 40–42, 48–52; 128/898; 607/88, 89, 93, 96, 98–104, 108
See application file for complete search history.

(56) References Cited

U.S. PATENT DOCUMENTS 4,976,709 A * 12/1990 Sand .............................. 606/5
5,529,076 A * 6/1996 Schachar .................... 128/898

* cited by examiner

*Primary Examiner*—David M. Shay
(74) *Attorney, Agent, or Firm*—Colin P. Abrahams

(57) ABSTRACT

Methods and apparatus are provided that prevent or inhibit functional regression caused by the stromal remodeling resulting from epithelial or fibroblastic apoptosis or necrosis in patients who will undergo or have undergone a thermal ciliary muscle tendinoplasty or scleral collagen shrinkage procedures. Methods and compositions are provided that prevent apoptosis in epithelial cells by stromal cooling during thermal tendinoplasty procedures; that create or restore stabilizing molecular cross-links between scleral stromal lamellar fibers; and that interrupt at least one step in the stromal remodeling response including inhibition of apoptosis, fibroblastic proliferation and migration, and inhibition of collagenesis.

30 Claims, 8 Drawing Sheets

Nonhydroxylated Procollagen

+ Prolyl Hydroxylase

Hydroxylated Procollagen

α₁     H-Gly-Tyr-Asp-Glu-Lys-Ser-Ala-Gly-Val-Ser-Val-Pro-Gly-

α₂     PCA-Tyr-Ser-Asp-Lys-Gly-Val-Ser-Ala-Gly-Pro-Gly-Pro-

α₃     H-Gly-Tyr-Asp-Glu-Lys-Ser-Ala-Gly-Val-Ser-Val-Pro-Gly-

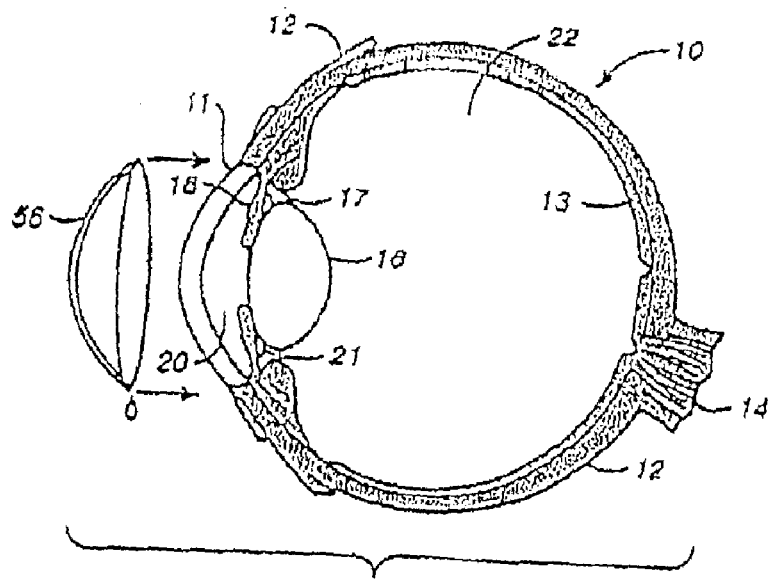
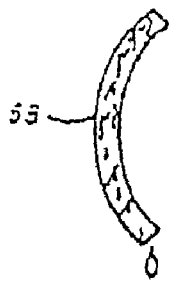 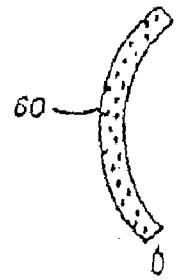 
FIG. 8a
FIG. 8b     FIG. 8c     FIG. 8d
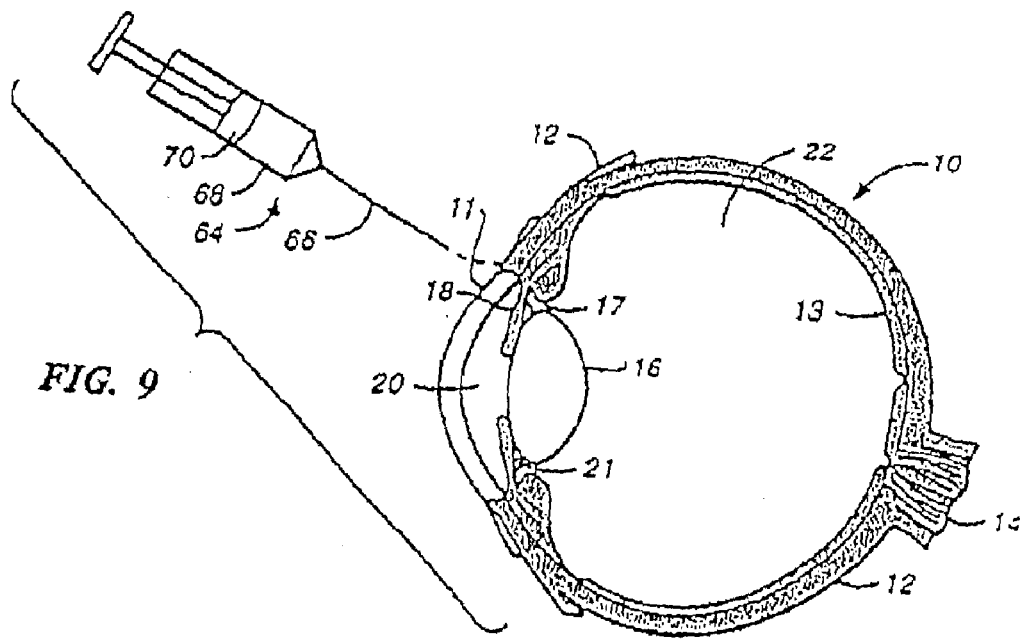
FIG. 9

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Purchased commercially or sequence is
      synthesized

<400> SEQUENCE: 1

Gly Tyr Asp Glu Lys Ser Ala Gly Val Ser Val Pro Gly

<210> SEQ ID NO 2
<211> LENGTH: 12
<212> TYPE: PRT
<213> ORGANISM: Artificial Sequence
<220> FEATURE:
<223> OTHER INFORMATION: Purchased commercially or sequence is
      synthesized

<400> SEQUENCE: 2

Tyr Ser Asp Lys Gly Val Ser Ala Gly Pro Gly Pro
```

PREVENTION OF REGRESSION IN THERMAL CILIARY MUSCLE TENDINOPLASTY

CROSS REFERENCE TO RELATED APPLICATIONS

This application is a continuation-in-part of U.S. patent application Ser. No. 10/229,762 filed Aug. 28, 2002, which is a continuation in part of U.S. patent application Ser. No. 10/113,361 filed Mar. 29, 2002 now abn, which application claims the benefit of United States Provisional Applications Nos. 60/280,670 filed Mar. 30, 2001 and 60/311,518 filed Aug. 11, 2001, all of which are incorporated herein by reference in their entirety.

BACKGROUND OF THE INVENTION

Collagen shrinking processes have been used in clinical medicine for various applications. In orthopedics and sports medicine, both laser and radio frequency methods have been utilized for generating the temperature elevation required for collagen phase transition in unstable joint disease and other orthopedic conditions. In otology, lasers have been used to increase the structural integrity of the tympanic membrane in a condition of presbycusis whereby the ear drum becomes somewhat flaccid resulting in hearing impairment in the vocal range.

Thermal keratoplasty, another collagen shrinkage modality, is now an accepted refractive surgical process for altering the front surface radius of the cornea in the treatment of hyperopia. Both radio frequency and coherent energy are utilized in the thermal phase transition, which results in the stromal collagen shrinkage.

A novel process, which remedies the loss of amplitude and range of focus in presbyopia, has been disclosed in previous filings. A collateral benefit of this process applies to the treatment of glaucoma and ocular hypertension. This process also utilizes collagen shrinkage targeting the collagenous ciliary muscle tendon and sclera.

In each application of collagen shrinkage to derive a beneficial effect, permanence of effect has been elusive due to wound repair processes incited as an adjunctive event in each application. Loss of effect as a function of time, otherwise known as regression of the desired effect, has been shown to result from the wound repair process. Regression has, therefore, been a significant problem, which has frustrated attempts to design procedures that are both efficacious and predictable, while remaining safe.

It then would seem to be advantageous to be able to control, ameliorate, and/or obtund this wound repair cascade during and following these various collagen shrinkage processes. The management of these repair events would predispose to long term and, possibly, permanent beneficial results resulting from the collagen phase transition.

All attempts to alter the refractive surfaces of the cornea are, by their very nature, an alteration of the integrity of the corneal tissue. Each method of corneal recurvature requires some mode of traumatic intervention, although some methods are more invasive than others. As one creates ever more complex radius modification upon the anterior surface or within the corneal stroma, the trauma is compounded. In view of this trauma, the efficacy and predictability of each method becomes an important issue.

Interactive wave front-guided refractive modification has been integrated into the process in an attempt to diminish the aberrations generated by the various refractive surface in the image path. While this modality has the advantage of improving the visual result of refractive intervention, this process does nothing to ameliorate the wound repair cascade. Refractive regression will still be related to the change in tissue structural bio-mechanics induced by the trauma.

Observations of the post-operative corneal radius creep and deformation have elicited an understanding of the changes that affect the stability and predictability of the desired effect. Some of the changes seen in regression are indeed, paradoxical, while others appear to be directly related to the type of trauma sustained. The molecular and cellular biological responses manifested by these processes are the result of several separate, but integrated events. These events include, but are not limited to cellular apoptosis, cellular necrosis, accumulation of stress or heat shock proteins, and destruction of the lamellar-stabilizing molecular cross-links.

Current treatments, which reduce the fibrosis and scarring that accompanies wound repair, include antimetabolites, immunosuppressants, corticosteroids, and various cytokines or growth factors such as TGF-$\beta$. These methods have been used to reduce or prevent corneal haze in refractive surgery. Mitomycin C, an anti-cancer drug, has been used for this purpose, but this drug does not address the complex issues associated with the wound repair cascade. Mitomycin C is a toxic drug, which can cause serious collateral complications and caution must be observed in its use.

Refractive keratoplasty is defined as any interventional process by which the corneal front radius of curvature is altered to improve visual refractive function.

A need clearly exists to find a way to prevent the regression that characterizes so many collagen shrinkage processes with special reference to thermally mediated processes addressing the treatment of presbyopia and the collateral treatment of chronic open angle glaucoma.

In one aspect, this invention discloses methods and devices for preventing the wound repair cascade, and subsequent loss of effect, in the treatment of presbyopia, in the treatment of the loss of the range and amplitude of accommodation, in the treatment of chronic open angle glaucoma, and in the treatment of ocular hypertension by collagen shrinkage modalities.

SUMMARY OF THE INVENTION

The methods and compositions of the present invention provide therapeutic agents designed to accurately intersect with certain stages of the scleral wound healing process and inhibit the repair mechanisms that contribute substantially to regression of desired effect in the treatment of presbyopia, the treatment of reduced amplitude and range of accommodation, the treatment of ocular hypertension and the treatment of chronic open angle glaucoma.

Also disclosed is a method of preventing or inhibiting loss of desired effect of the shrinkage of the ciliary muscle tendon and sclera, where the loss of effect is caused by scleral stromal remodeling. This method comprises interrupting at least one step in the stromal remodeling response by providing an effective amount of a composition that modulates the step, where the interrupted step results in inhibition of apoptosis, inhibition of cellular necrosis, inhibition of glycosaminoglycan synthesis, or inhibition of collagenesis.

The step inhibited can be the cascade associated with Connective Tissue Growth Factor (CTGF) or biologically active fragments thereof, and can be an antibody or fragment thereof, a nucleic acid or other molecule, which inhibits the expression of the gene or protein, or one which blocks a receptor of CTGF. Alternatively, the composition can be an antibody/fragment, chemical compound, or nucleic acid that inhibits the accumulation of the heat shock protein-70 and result in an inhibition of collagen assembly to its properly folded state, or inhibits the effects of C-proteinase in stromal remodeling, or the effects of prolyl hydroxylase. Preferred inhibitors of prolyl hydroxylase include FG-16648 and FG-O41 (proprietary compounds of Fibrogen, Inc., South San Francisco, Calif.). An advantage of this method lies in that it disrupts one or more phases of fibrosis and wound repair cascade pharmacologically without disrupting all phases of fibrosis and wound repair, thus selectively preventing specific causes of regression of effect.

Another disclosed method of preventing or inhibiting a loss of collagen shrinkage as a function of time comprises applying an effective amount of a composition that creates or restores cross-links between stromal lamellae, where the cross-links increase the stability of the scleral stroma. Compositions of the method preferably create or restore hydrogen bonds, electrostatic forces, or covalent bonds between the lamellar fibers. A preferred composition is glycerol or glucose, which requires no heat or light activation to induce cross-links. Other preferred compositions include photoactivable substances, and when these are used, the method further comprises applying photo-irradiation to target tissue after application of the composition to activate the composition and create cross-links. A preferred photoactivable composition is riboflavin, which is activated by heat to form cross-links.

Another feature of the invention is a composition comprising an agent and an excipient capable of combining with the agent and carrying across the scleral target tissue. In preferred embodiments, the composition further comprises a topical ocular insert, which serves as a reservoir and delivery device for the agent. Preferred inserts include pleggets, polymer contact lenses soaked in the agent, collagen shields impregnated with the agent, and liposomes, flexible capsules, or flexible wafers containing the agent, or other membrane or reservoir systems. The agent and excipient are preferably efficacious and bio-available in doses practical to administer to the eye, and are non-toxic and physiologically compatible with the eye. Preferably the agent is an antibody, a small molecule, or a nucleic acid, more preferably an antibody against CTGF or a fragment thereof, an antibody against prolyl hydroxylase or a fragment thereof, an antibody against hsp-70 or a fragment thereof, or an antibody against C-proteinase or a fragment thereof.

Another feature of the invention is a composition for preventing or inhibiting regression which comprises an agent that creates or restores intermolecular cross-links between lamellar fibers in the scleral stroma, and an excipient capable of combining with the agent and carrying it across the target tissue and that is physiologically compatible with the eye. Preferably, the agent comprises glycerol or glucose. In preferred embodiments, the composition further comprises a topical ocular insert, which serves as a reservoir and delivery device for the agent. Preferred devices include pleggets, polymer contact lenses soaked in the agent, collagen shields impregnated with the agent, and liposomes, flexible capsules, or flexible wafers containing the agent, or other membrane or reservoir systems. The agent and excipient are preferably efficacious and bio-available in doses practical to administer to the eye, and are non-toxic and physiologically compatible with the eye. Preferably, the agent is an antibody, a small molecule, or a nucleic acid.

DESCRIPTION OF THE DRAWINGS

FIGS. 8a–8d demonstrates application of drug reservoirs such as soft contact lenses (8a), pledgets (8b), sponges (8c), flexible capsules, wafers, or other membrane or reservoir systems (8d).

FIG. 9 illustrates subconjunctival injection.

DETAILED DESCRIPTION OF THE INVENTION

Figure 1:
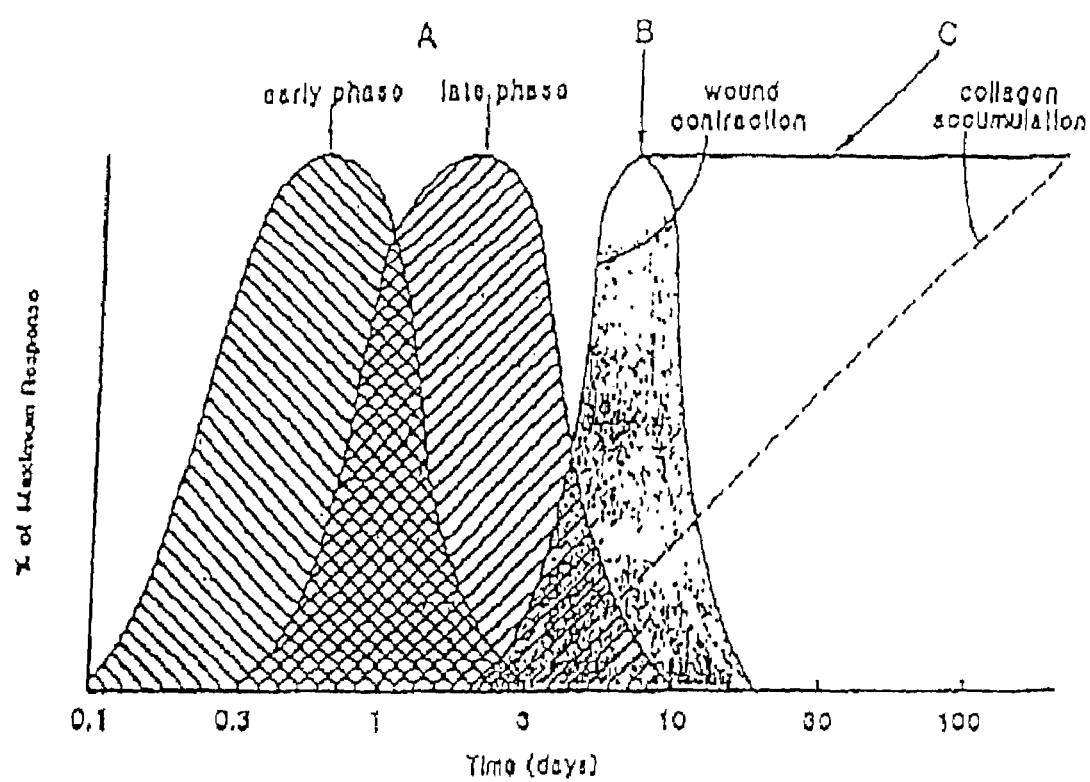
FIG. 1 is a graph showing the overlapping phases of wound repair, where (A) is the inflammation stage (early and late), (B) is re-epitheliazation and granulation tissue formation, and (C) is matrix formation and remodeling. Collagen accumulation begins shortly after the onset of granulation tissue formation.

It has been discovered that prevention of epithelial apoptosis and/or modulation of the wound healing process at selected points, particularly stromal remodeling, can inhibit or prevent the process of regression following collagen shrinkage ciliary muscle tendinoplasty. The wound and wound repair processes affected by the methods and compositions of the invention include epithelial and fibroblastic apoptosis and necrosis, and the disruption of the stromal lamellae of the sclera. These processes lead to loss of the desired functional result, and the prevention of any of the processes, or particular manifestations, such as the accumulation of heat shock proteins, fibrillogenic response of wound repair, or repair of stromal cross-links, can prevent or inhibit the loss of collagen shrinkage changes and regression of the desired effect. In addition, a novel method of thermal quenching during this process of heat induced collagen shrinkage is disclosed that reduces the apoptosis associated with the thermal damage, thus reducing the subsequent wound healing response. This method, alone or in combination with the wound healing inhibition and remedial cross-linking methods herein disclosed, is designed to reduce the amount of functional regression experienced by patients who have undergone these procedures.

An important component of the invention is concerned with regression accompanying laser and radio-frequency modulated collagen shrinkage techniques, such as ciliary muscle tendinoplasty. The biological responses to trauma and the wound repair cascade following these thermally mediated procedures are becoming better understood, as is their relationship to functional regression of effect. Apoptosis and direct cellular necrosis induces the wound repair response in each case. Damage to the stabilizing molecular cross-links also occurs with each method. These processes are induced and integrated during the various techniques for collagen shrinkage and tend to reverse the desired effect generated by the thermally mediated process.

1. Control of Thermal Injury During Photothermal Tendinoplasty

In the various methods commonly used today, thermal effects are an important means of modifying the scleral collagen properties. Because coupled radiative-thermal effects are present during and after pulsed irradiation by laser or radio frequency energy, determination of the optical and/or the thermal properties of the test material can be complex. For example, if the irradiation of the tissue is repeated before the tissue completely cools, the elevation of the tissue temperature is additive. When, however, the repetition rates are fast, the pathophysiological effects of pulsed laser irradiation can be essentially like those produced by continuous wave lasers. The pathologic changes of thermal injury can be placed into temperature-time categories in increasing order of severity. The tissue response to injury or the wound repair response thus also varies.

A. Methods to Regulate Energy Dose for Optimal Shrinkage Effects and to Minimize Damage.

(i) Calculation of Thermal Effects

An understanding of the photothermal tissue effects from lasers emitting in the infrared has led to the study of pulsed photothermal radiometry (PPTR). PPTR is a technique for determining tissue reaction with reference to its thermal properties. PPTR has been investigated as an indirect modality for determining the appropriate laser treatment for various tissue, such as skin, tendon and cornea.

Photothermal effects are produced within the target tissue when, by means of the appropriate laser exposure parameters, the radiant energy exceeds the threshold required for tissue modification. The photothermal changes trigger a biological response which culminates in a complex sequence of events within the irradiated tissue. These changes may be only represented by a phase transition or may proceed to tissue destruction with a wound healing response and new tissue synthesis. In any case, the definitive change will be determined by the magnitude of the thermal response, or the "thermal history" of the tissue.

PPTR is a non-contact method that uses a rapid acting infrared detector to measure the temperature changes induced in a test material exposed to pulsed radiation. Heat generated as a result of light absorption by subsurface chromophores in the test material diffuse to the surface and results in increased infrared emission levels at the surface. By collecting and concentrating the emitted radiation onto an infrared detector, one obtains a PPTR signal that represents the time evolution of temperature near the test material's surface. Useful information regarding the test material (e.g. corneal or skin tissue) may be deduced from analysis of the PPTR signal.

Experiments have been conducted at the Beckman Laser Institute (University of California, Irvine) to determine depth profiles of laser light absorption in skin tissue. It has been discovered that strong scattering compared with absorption tends to raise the front surface temperature, as some of the scattered light is absorbed while back-scattering through the front surface. If the scattering is a significant event, the radiation transport, temperature distribution and penetration depth are all primarily dominated by the scattering and not by the chromophore absorption.

When the desired endpoint is collagen stress compaction or hydrothermal shrinkage, as in photothermal tendinoplasty, an appropriate thermal profile within the therapeutic window must be attained. Collagen phase transition from the tightly wound triple helical form to the relaxed contracted form begins as the tissue temperature reaches about 55° C. If a sufficient volume of tissue does not reach that collagen shrinkage, changes do not occur. If the temperature exceeds 68° C., collagen denaturation proceeds to destruction. The contracted state then regresses, as does the desired function result.

PPTR is a novel method, when combined with infrared pulsed laser irradiation, to determine objective patient-specific laser treatment conditions. When combined with front surface cooling or the conduction of heat away from the front surfaces (discussed below), it provides an even more refined ability to determine and exquisitely control the laser generated thermal profile within the scleral tissues. Superficial tissue cooling processes may be either static as in the form of a simple heat sink, or dynamic as in the addition of an evaporative cooling agent. PPTR permits patient-specific determinations with or without additional cooling capabilities.

One design of the thermal monitoring system embodies the use of a rapid acting thermal sensor that is focused upon the delivery site of the laser. The steady state tissue temperature is obtained and integrated with the known or experimentally determined thermal gradient between he surface and the subsurface target tissue after sub-threshold radiant exposure. Computing electronics within the laser system can automatically determine the appropriate dosimetry.

This system can be applied to any coherent or non-coherent light source, as well as to radiofrequency energy sources used to perform any beneficial treatment within the human body that is dominated by thermal or photothermal biological mechanisms.

When integrated with a dynamic cooling system, when the superficial temperature decrease resulting from evaporative cooling is not within programmed range, as in the case of reduced level of cryogen within the coolant reservoir, the laser operation will not be enabled, providing a fail-safe operation. This control allows the surgeon to effect the scleral change in the desired temperature range without risking collagen denaturation caused by accidental overheating.

(ii) Dynamic Cooling Methods

Inasmuch as thermal injury to the scleral epithelium in laser and radiofrequency conductive tendinoplasty causes secondary fibroblastic apoptosis immediately beneath the irradiated sites, a novel dynamic cooling process is presented to protect the epithelium from damage. This procedure is referred to as "thermal quenching". A similar procedure has been used in aesthetic dermatology to protect the epidermis while an infrared laser achieves thermal denaturation of the proteins in the papillary and reticular dermis to reduce rhytides or superficial cutaneous wrinkles. A modification of this procedure is disclosed that allows the cooling method to be used in ciliary muscle tendinoplasty.

It has been discovered that appropriate application of pulsed laser irradiation and cryogen spray cooling may be used to protect the scleral epithelium and selectively confine the spatial distribution of thermal injury to the stroma. The ability to limit preferentially spatial distribution of thermal injury is supported by histological studies in an animal model (Milner et al. JOSA A 12:1479–1488 (1995); Anvari et al., Phys Med. Biol., 40:241–252 (1995)).

In this procedure, the epithelium is rapidly cooled prior to pulsed laser irradiation by a short, gentle spurt of cryogen sprayed upon the scleral surface. Subsequent absorption of pulsed laser energy by water in the scleral stroma results in a temperature increase sufficient to cause spatially selective protein denaturation and phase-transition or shrinkage. Because epithelial temperature at superficial depths is decreased by dynamic cooling, thermal injury in the epithelium is reduced or eliminated.

In an alternate embodiment, this technology can be used to pre-cool a sapphire contact lens or lens, which would transmit 100% of the coherent thermal energy to the stroma while the contact lens acts as a heat sink to conduct heat away from the superficial sclera, thus preventing thermal trauma and the subsequent apoptotic fibroblast death. This process is a combination static-dynamic cooling process which can be temporally integrated with the laser irradiation.

B. Prevention of Apoptosis from Thermal Trauma

There appears to be a correlation between fibroblastic apoptosis and scleral thermal trauma occurring during ciliary muscle tendinoplasty. Studies elucidating this correlation have suggested the use of various pharmacologic and mechanical methods in the modulation of this biological response. The goal is to prevent, control or eliminate the apoptosis and the wound healing response that is stimulated by the apoptosis that is responsible for these regressive changes.

This fibroblast destruction precipitates a wound repair process culminating in the synthesis of glycosaminoglycans (GAG's) and collagen. It is desirable to inhibit this process before it is precipitated. Conduction of heat away from the scleral epithelial surfaces will prevent the epithelial destruction during thermal tendinoplasty. It is the epithelial damage which causes the epithelial-stromal interaction precipitating the apoptotic fibroblast death seen in laser tendinoplasty.

The process of thermal quenching is applicable to scleral tendinoplasty as discussed above. Various methods of thermal quenching are efficacious and include both passive and dynamic cooling of the scleral epithelial surface.

Static cooling may be accomplished by means of a contact device which transmits the IR radiation used in the thermal tendinoplasty such as 2 micron THC:YAG irradiation, but has enough thermal mass to serve as an efficient heat-sink to the scleral epithelium. Such materials include sapphire and quartz. The sclera is best served if the contact device has a base curve parallel to or flatter than the flattest radius of the sclera. Pre-cooling of the device can be done.

Dynamic cooling or thermal quenching can be accomplished by spraying the cornea with a cryogen, such as 1,1,1,2 tetrafluoro-ethane® 134a according to the National Institute of Standards and Technology; boiling point approximately −26° C.). As it rapidly evaporates, the corneal surface cools. The longer the cryogen is in contact with the epithelium, the deeper the cooling effect. Therefore, a short burst of the magnitude of 5 milliseconds or less by a fine mist is efficacious. The finer the mist, the more rapid the evaporation from the surface. The infrared laser irradiation would be automatically enabled following the spray application.

The timing of the application of the contact device or cryogenic spray precedes the laser irradiation. In this way, the epithelium is rendered hypothermic, thus protecting it from destruction as the photothermal energy is transmitted through and absorbed by the universal chromophore, water, within the stroma.

2. Modulation of the Wound Healing Response to Inhibit Regression of Effect.

It is an aspect of the invention to interrupt the process of repair undertaken by the sclera so that it does not revert to its original (pre-surgical) shape and condition.

A. Phases of Wound Repair

Wound repair is an integration of dynamic interactive processes. In the absence of intervention, these wound repair processes follow a specific time sequence and can be temporally categorized into three phases: (A) inflammation, (B) tissue formation, and (C) tissue remodeling.

These phases of wound repair are not mutually exclusive, but rather overlap in time (FIG. 1), and are roughly as follows:

(i) Inflammation (Early and Late)

(1) blood vessel disruption with concomitant extravasation of blood constituents.

(2) blood coagulation and platelet aggregation generate fibrin-rich clot.

(3) provides matrix for low impedance cell migration.

(4) platelets secrete growth factors that initiate granulation tissue formation.

(5) neutrophils attack foreign bodies.

(6) monocyte infiltration continues and promotes phagocytosis.

(7) monocytes change into reparative macrophages which secrete growth factors.

(ii) Granulation Tissue Formation (1) begins to form in 4 days.

(2) consists of new vessels, macrophages, fibroblasts and loose connective tissue.

(3) fibroplasia consists of granulation tissue components (fibroblasts and extracellular matrix (ECM)).

(iii) Matrix Formation and Remodeling (1) structural molecules of early ECM contribute to tissue formation by providing a scaffold for fibronectin and collagen, low impedance cellular mobility and reservoir for cytokines.

(2) cytokines stimulate fibroblasts to migrate and switch their major role to protein (collagen) synthesis.

(3) fibroblasts participate in ECM remodeling, e.g., by depositing fibronectin as a second-order provisional matrix (the appearance of fibronectin, then collagen in healing wounds is consistent with fibronectin, serving as a template for collagen fibril organization).

(4) hyaluron is a major component of early granulation tissue, promoting cellular movement.

(5) proteoglycans are secreted by the ECM and mature fibroblasts; their function in the ECM is to regulate collagen fibrillogenesis.

(6) collagen fibrillar deposition into the wound site peaks around 7 to 14 days and provides the structural support.

(7) myofibroblasts differentiate and cause tissue contraction by means of dynamic linkages between actin bundles and ECM.

(8) by the third week, wounds gain about 20% of their final strength.

(9) collagen remodeling during the transition of granulation tissue to mature scar is dependent upon both continued collagen synthesis and collagen catabolism controlled by a variety of enzymes.

FIG. 1 shows these wound repair processes plotted as a logarithmic function of time. The phases of wound repair overlap considerably with one another. Inflammation is divided into early and late phases denoting neutrophil-rich and mononuclear cell-rich infiltrates, respectively. Wound contraction begins after granulation tissue is well established. Collagen accumulation begins sharply after the onset of granulation formation.

These processes are generally mirrored in ocular histopathology, except for the vascular events which are modified in the cornea due to its avascularity. Several general cellular and molecular events are precipitated by traumatic scleral intervention; (1) apoptosis, or programmed cell death, (2) necrosis from direct cellular destruction, (3) lamellar instability, which is caused by damage to the stabilizing intermolecular and intra-molecular collagen cross-links within the collagen matrix, and (4) accumulation of heat shock proteins. Epithelial hyperplasia may also play a role, but this appears to be precipitated by apoptosis.

B. Apoptosis

Apoptosis differs from cellular necrosis, in which the cell contents including the proteolytic enzymes are released into the surrounding area and stimulate an inflammatory response and further damage. Apoptosis is a programmed cell death process in which the cells die in a complex and controlled way with minimal collateral tissue damage or inflammation. Apoptosis occurs when the scleral procedure is accompanied by injury to the scleral epithelium, during which various growth factors or cytokines are released from the injured epithelial cells. Among these growth factors are interleukin-1 (IL-1), α and β, and FAS ligands. The cytokines diffuse into the stroma and, thereby, bind to specific receptors located on the cellular surface of the stromal fibroblast-like cells.

Interleukin-1 α binds to IL-1 receptor type 1, thus modulating epithelial-stromal communications. This leads to fibroblast disappearance beneath the epithelial injury site. The increased levels of IL-Ia and IL-1b induce apoptotic death of fibroblasts in the stroma.

FAS ligand (FasL) is a membrane-bound protein, which also induces apoptotic cell death in cells expressing the FAS receptor. All fibroblasts to a depth of 50% of the stroma (200 microns) or more may die, depending upon the type of epithelial injury. The morphologic changes in the stromal apoptotic fibroblasts include chromatin shrinkage and fragmentation, cell shrinkage and cellular blebbing of apoptotic bodies. Because the highly organized structure of the stroma is essential for the proper propagation of light though the sclera, the elimination of fibroblasts induced by the epithelial trauma can result in stromal haze such as that observed after various thermal procedures.

It now appears that these cytokine systems are interrelated. Without wishing to be bound by a mechanism, evidence shows that the IL-1 release from the damaged epithelial cells facilitates expression of FasL mRNA and protein at the time that cell death in response to IL-1α is noted. It appears that IL-1 may trigger autocrine suicide of fibroblasts by induction of FAS ligand in cells already expressing the FAS receptor. It thus, appears that several systems may mediate fibroblast apoptosis in response to the epithelial wounding.

This interaction then induces fibroblasts to up-regulate hepatocyte growth factor (HGF), keratinocyte growth factor (KGF), and protein levels, all of which aid in the wound remodeling. For example, HGF and KGF both stimulate epithelial cell proliferation. Concurrent stimulation of proliferation and inhibition of differentiation in epithelial cells can produce thickening of the epithelium and hyperplasia. Epithelial hyperplasia has been shown to be another factor that leads to regression of functional effect (see, e.g., Spadea et al., J. Refractive Surgery, 16:133–139 (2000); Salchow et al. J. Refractive Surgery, 15:590–593 (1999), both herein incorporated by reference).

The destruction and removal of the apoptotic cells stimulates the migration of new fibroblasts from the posterior and peripheral stroma to the site of injury in the anterior stroma. These repopulating fibroblasts differ in appearance from the apoptotic cells in that they have dark nuclei and prominent intracellular organelles, and are indistinguishable from fibroblasts in other parts of the body. These activated fibroblasts are associated with the increased stromal collagen synthesis and collagen disorganization accompanying stromal remodeling (correlating with the increased haze as seen in excimer photorefractive keratectomy) and the regression of effect or corneal topographic hysteresis as observed in all refractive surgical procedures.

Fibroblastic apoptosis is, therefore, an initiating event in the wound healing response after the epithelial removal in PRK and/or thermal damage in photothermal keratoplasty and radio frequency keratoplasty. While somewhat diminished in laser-assisted in situ keratomileusis (LASTK), there is also a significant wound healing response within the stroma with the level of regression after LASIK varying from essentially zero to as much as 50% in individual cases. Interference during tendinoplasty with one or more steps in the apoptosis triggering mechanism, or with the migration of new fibroblasts into the recently remodeled sclera, can prevent the deleterious fibroblasts and/or collagenous matrix proliferation that leads to regression.

C. Cellular Necrosis

The wound repair-related regression in LASIK appears to be more the result of cellular necrosis inducing collagenesis and stromal remodeling than the result of cellular apoptosis and epithelial hyperplasia (as the epithelial damage in this procedure results only from the laser microkeratome). Cellular necrosis (not apoptosis) results from the ablation of the stroma. The necrotic cell's appearance differs from apoptotic cells and is characterized by the rapid loss of membrane function and abnormal permeability. There is early disruption of organelles and irreversible damage to mitochondria.

A histological study has revealed that the two cellular destructive processes are distinguishable from each other based upon staining and histological criteria in tissue specimens. Clinically, they both stimulate wound repair cascades culminating in collagenesis that in turn causes the regression of effect. This is also true of medicated ciliary muscle tendinoplasty.

D. Distinguishing Apoptosis from Cellular Necrosis

Standard, art-known H & E staining characteristics can be used for identification of necrosis and TUNEL stain can be used to identify apoptotic nuclei with their characteristic DNA fragmentation. Nuclear DNA fragmentation occurs relatively early in the process of apoptosis, preceding significant disruption of the nuclear membrane, but it is a relatively late event in necrosis, occurring when there is already severe nuclear and/or cellular membrane disruption. The TUNEL stain labels fragmented DNA and is not specific for either apoptosis or necrosis. Therefore, the presence of apoptotic cell death is determined by identifying cells stained by TUNEL that have an intact nuclear membrane. In contrast, necrotic tissue will stain positively in the TUNEL assay and display a disrupted nuclear membrane. The use of TUNEL to identify fragmented DNA, in conjunction with H & E staining of the nuclear membrane, provides that necrosis and apoptosis can be reliably distinguished, allowing for the separate analysis of each.

It now appears that the epithelial-stromal apoptotic responses and the post-necrotic wound repair processes each play important roles in the stromal remodeling responsible for the regression of effect. Both processes occur immediately after injury and may persist for long periods of time following the injury. Thus, they are prime targets for intervention to prevent regression.

E. Heat Shock or Stress Proteins—Relation to Prevention of Regression in Laser Thermal Tendinoplasty Immediately after a sudden increase in temperature, all cells increase production of a certain class of molecules. When first observed some 35 years ago, this phenomenon was called the "heat shock response". It is now commonly referred to as the stress response and the expressed molecules as stress proteins.

These proteins are far more than just defensive molecules. Throughout life of a cell, many of these proteins participate in essential metabolic processes, including the pathways by which other cellular proteins are synthesized and assembled. Some stress proteins appear to orchestrate the activities of molecules that regulate cell growth and differentiation.

The stress proteins do play an active role in cellular defense. For example, the stress response plays an important role in the ability of animals to withstand brief exposures to high temperatures. The stress response facilitates the identification and removal of denatured protein from the traumatized cell.

Many of the agents that induce the stress response are protein denaturants and can lead to loss of the protein's biological function. It has been suggested that the accumulation of denatured or abnormally folded proteins in a cell initiates a stress response. This response has been observed in the phase-transition precipitated by laser thermal keratoplasty.

A highly inducible heat shock protein, hsp-70, accumulates inside the nucleolus after heat shock. The nucleolus manufactures ribosomes, the organelles on which proteins are synthesized. After heat shock, cells stop making ribosomes and their nucleolus becomes awash in denatured ribosomal particles. Hsp-70 recognizes denatured intracellular proteins and restores them to their correctly folded, biologically active shape.

There is a family of hsp 70-related proteins. All of them share certain properties, including a high affinity for adenosine triphosphate (ATP). All of these related proteins, with one exception, are present in cells growing under normal conditions, yet in cells experiencing metabolic stress, they are synthesized at much higher levels.

It has been observed that one form of hsp-70 is identical to immunoglobulin binding protein (BiP). BiP is involved in the preparation of immunoglobulins, as well other secreted proteins. BiP binds to newly synthesized proteins as they are being folded or assembled into their mature form. If the proteins fail to fold or assemble properly, they remain bound to BiP and are eventually degraded. In addition, under conditions in which abnormally folded proteins are accumulated, the cell synthesizes more BiP.

Taken together, these observations indicate the BiP helps to orchestrate the early events associated with protein secretion. BiP seems to act as a molecular overseer of quality control, allowing properly folded proteins to enter the secretory pathway but holding back those unable to fold correctly.

Biochemical studies have indicated that other proteins known as hsp-10 and hsp-60 are also essential to protein folding and assembly. The hsp-60 molecule consists of two seven-member rings stacked one atop the other. This large structure appears to serve as a "work-bench" onto which unfolded proteins bind and acquire their final three-dimensional structure. According to current thought, the folding process is extremely dynamic and involves a series of binding and release events. Each requires energy, which is provided by the enzymatic splitting of ATP, and the participation of hsp-10 molecules. Through multiple rounds of binding and release, the protein undergoes conformational changes that take it to a stable, properly folded state.

It is likely that both hsp-60 and the hsp-70 families work together to facilitate protein maturation. As a new polypeptide emerges from a ribosome, it becomes bound to a form of hsp-70 in the cytoplasm. Such an interaction may prevent the growing polypeptide from folding prematurely. Once the synthesis is complete, the new polypeptide, still bound to its hsp-70 escort, is transferred to a form of hsp-60, on which folding of the protein and its assembly with other protein components commences. Hsp-60 and hsp-70 act as "molecular chaperones". Although the molecules do not convey the information for the folding or assembly of proteins, they do ensure that those processes occur quickly and with high fidelity. They expedite self-assembly by reducing the possibility that a maturing protein will head down an inappropriate folding pathway.

Temperatures that are sufficient to activate the stress response may eventually denature some proteins inside cells. Heat-denatured proteins, like newly synthesized and unfolded proteins, would therefore represent targets to which hsp-60 and hsp-70 can bind. Over time, as more thermally denatured proteins become bound to hsp-60 and hsp-70, the levels of available chaperones drop and begin to limit the ability of the cell to produce new proteins. The cell somehow senses this reduction and responds by increasing the synthesis of new stress proteins that serve as molecular chaperones.

A rise in the expression of stress proteins may also be a requirement for the ability of cells to recover from a metabolic insult. If heat or other metabolic insults irreversibly denature many cellular proteins, the cell will have to replace them. Raising the levels of those stress proteins that act as molecular chaperones will help facilitate the synthesis and assembly of new proteins. In addition, higher levels of stress proteins may prevent the thermal denaturation of other cellular proteins.

The magnitude of the resulting stress response appears to correlate with the relative severity of damage sustained. This has focused the utility of using the changes in stress protein levels as markers for tissue and organ injury. Our preclinical studies to develop an animal model for photothermal trauma has utilized this principle in determining appropriate markers of laser-induced trauma.

Cells that produce high levels of stress proteins appear better able to survive ischemic damage than cells that do not. Consequently, raising the levels of stress proteins, for example by pharmacological means, may provide additional protection to injured tissues and organs. For example, raising the levels of such proteins prior to refractive keratoplasty could lead to protection from apoptosis of keratocytes following the procedure. A corollary to this principle is applicable to the inhibition of the cascade responsible for corneal stromal remodeling that results from interventional laser refractive keratoplasty. Thus, lowering the levels of stress proteins produced would limit stromal remodeling by impairing the expression or secretion of collagen.

F. Control of Stromal Remodeling

Stromal remodeling is one of the important factors in tendinoplasty regression. The wound healing process that results in the remodeling is a complex cascade of events which, in most cases, is hematogenous in origin. An exception to this is the response to injury in the cornea, which is an avascular tissue.

Collagenesis, the culmination of all tissue regeneration or healing, progresses naturally from the migration of the multi-potential fibroblast into the wound sites. Fibroblasts differentiate and are guided by a chemotactic gradient into the provisional matrix-filled wound space. An active proteolytic system also cleaves a way for the fibroblast migration.

After the fibroblast has migrated into the wound, it gradually switches its major function to synthesis of great quantities of collagen in response to TGF-β. Once an abundant collagen matrix is deposited in the wound, the fibroblasts cease collagen production, despite the continuing expression of TGF-β. Signals responsible for down-regulating fibroblast proliferation and matrix synthesis may include factors such as gamma-interferon and the collagen matrix itself (suppressing both fibroblast proliferation and fibroblastic collagen synthesis). A complex interaction and feedback control between cells-cytokines/growth factors-enzymes-matrix is what controls the production of collagen.

Hyaluronic acid (a glycosaminoglycan or GAG) appears to promote cellular migration in early granulation tissue and as it becomes hydrated, it promotes expansion of the interstitial spaces, allowing more cell recruitment and proliferation in these areas. Once the wound is filled with granulation tissue and covered with neo-epidermis, myofibroblasts differentiate to contract the wound, and epithelial cells differentiate to establish the permeability barrier.

The role of TGF-β in scar formation is not well understood, but this is where certain prior art methods to control the fibrotic response have been directed. These methods are very non-specific. TGF-β suppresses the proliferation of epithelial cells, which, by suppressing re-epithelialization of denuded basement membrane, may potentiate scarring and fibrosis that appear to be initiated in the absence of efficient re-epithelialization; and this growth factor has quite profound inhibitory activities on cells on the immune system. Hence, by suppressing the accumulation and/or activation of T-cell sub-population, TGF-β may also indirectly potentiate tissue scarring and fibrosis.

(i) Anti-Fibrotic Therapeutics

Fibrosis takes many forms and is the result of diverse causes. However, each of the many fibrotic diseases and disorders involves an excessive deposition of collagen and the accumulation of scar tissue. Scar tissue is composed of dense and inelastic collagen fibers. As a consequence, the formation of scar tissue causes the distortion and loss of normal histology and function. Regardless of the underlying cause, the cascade resulting in fibrotic tissue is the same. Currently available pharmacologically based treatments for fibrotic disorders are not very effective in preventing the pathological progression of fibrosis. However, recent advances in cell and cytokine biology have brought a new understanding of the molecular events underlying tissue fibrosis and reveal promising new therapies.

This invention takes advantage of these new developments to remedy the consequences of biological response to trauma in ocular pathology, not particularly with respect to scar formation, but rather with a view to limiting and/or preventing refractive regression of the cornea. Tissue engineering studies have resulted in the development of selective and focused compounds which inhibit collagen repair mechanisms, and human neutralizing antibodies which block the fibrogenic cascade.

Targets for this inhibition of effect include: (1) Heat Shock Protein 70 (hsp-70), (2) fibrogenic cytokines (CTGF), (3) intra-cellular collagen synthesis enzymes (prolyl hydroxylase) and (4) extra-cellular collagen fibrillar assembly enzymes (C-proteinase). Encouraging preclinical data on these programs has validated the molecular targets.

(a) Inhibition of Heat Shock Proteins

The various laser-assisted modalities for thermal shrinkage of collagen and phase transition, induce traumatic stress, resulting in the accumulation of high levels of stress proteins. The fibrillogenesis of these new proteins culminate in stromal remodeling and a reversal or regression of the desired functional change. Therefore, pharmacological inhibition of these stress proteins facilitates enhancement and predictability of this change by reducing the action of these molecular chaperones. Regression of the tendinoplastic modification as a function of time is thus prevented as well.

When these cells experience metabolic stress and produce more stress proteins, they also make a reporter enzyme which can be detected by various assays. Small molecule inhibitors or neutralizing antibodies to the stress proteins and/or their reporter enzyme(s) prevents their activity in the same way specific inhibitors are used prevent the fibrogenic cascade. Such antibodies and inhibitors provide specific therapeutics designed to block refractive regression. An example of a commercially available antibody is anti-hsp-70 from StressGen, Inc. ((800)661-4978, Victoria, British Columbia, Canada).

(b) Inhibition of Connective Tissue Growth Factor (CTGF)

As one studies the therapies which block the cascade of fibrogenic cytokines that drive the destruction of the ocular structure and visual function, it becomes obvious that no satisfactory therapies exist for these indications. Particularly interesting therapeutic candidates are antibodies and compounds which block the production of specific growth factors that enhance connective tissue growth. Excess accumulation of extracellular matrix and fibrosis in ocular disease processes has focused attention upon the role of certain fibrogenic cytokines or growth factors.

Growth factors are a class of secreted polypeptides that stimulate target cells to proliferate, differentiate and organize in developing tissues. The action of growth factors is dependent upon their binding to specific receptors which stimulate a signaling event within the cell. Examples of well-studied growth factors include platelet-derived growth factor (PDGF), insulin-like growth factor (IGF-1), transforming growth factor beta (TGF-β), transforming growth factor alpha (TGF-α), epidermal growth factor (EGF), and fibroblast growth factor (FGF).

PDGF is a cationic, heat-stable protein found in the alpha-granules of circulating platelets and is known to be a mitogen and a chemotactic agent for connective tissue cells such as fibrolasts and smooth muscle cells. Because of the activities of this molecule, PDGF is believed to be a major factor in normal wound healing and may contribute to such diseases as atherosclerosis and fibrotic diseases. PDGF is a dimeric molecule consisting of an A chain and a B chain. The chains form heterodimers or homodimers, and all combinations isolated to date are biologically active.

Studies on the roles of various growth factors in tissue regeneration and repair have led to the discovery of PDGF-like proteins. These proteins share both immunological and biological activities with PDGF and can be blocked with antibodies specific to PDGF. These new growth factors likely play a significant role in the normal development, growth and repair of human tissue. Therapeutic agents derived from these molecules may be useful in augmenting normal or impaired growth processes involving connective tissues in certain clinical states, e.g., wound healing. When these growth factors are involved pathologically in diseases, therapeutic developments from these proteins may be used to control or ameliorate uncontrolled tissue growth. Various cell types produce and secrete PDGF and PDGF-related molecules. In an attempt to identify the type of PDGF dimmers present in the growth media of cultured endothelial cells, a new growth factor was discovered. This previously unknown factor, termed Connective Tissue Growth Factor (CTGF), is related immunologically and biologically to PDGF, but it is the product of a distinct gene. CTGF (MW=34,000) is one of the CCN family of early response genes. CCN, an acronym for a family of genes related to connective tissue growth factor, derives its name from the CYR61, CTF and NOV growth factors.

CTGF stimulates matrix production and the proliferation of cells. CTGF does not substitute for TGF-β, which appears to prepare fibroblasts for responding to CTGF, but can supplement the action of TGF-β in inducing cell growth. CTGF is a heparin binding growth factor which may be involved in the activation and tissue storage of TGF-β (Kothapalli et al., Cell Growth & Differentiation, 1997). The TGF-β response element in the CTGF promoter confers the CTGF gene's responsiveness to TGF-β (Grotendorst et al., Cell Growth & Differentiation, 1996). Cells exposed to TGF-β produce CTGF, and this response can be used in a high throughput screen for compounds that block this pathway. Alternatively, since CTGF binds to at least two classes of receptors, small molecule agonists or antagonists can be developed using screening methods known in the art, and CTGF's activity modulated at the receptor-binding step in the cascade.

(1) Active Fragments of CTGF

Sequence data from other studies have identified an active fragment of CTGF, referred to as the EENI fragment (MW=10,000), a C-terminal protein of CTGF. Current data suggest that this and other CTGF fragments are produced by proteolytic cleavage. Biological activity is associated with the fragments as well as the intact molecule. The data are consistent with distinct regions of the CTGF molecule inducing different responses (proliferation vs. matrix induction) following proteolysis by different cellular receptors. It has been further suggested that enhanced proteolytic cleavage of CTGF is a progression factor enhancing the local fibrotic response. Antibodies have been developed and optimized to neutralize the various activities of CTGF, and these antibodies or other specific antibodies and small molecules can also be used to inhibit refractive regression.

(2) Specific Anti-CTGF Therapeutic Targets a) Human Monoclonal Antibodies which Neutralize CTGF or its Receptor High affinity fully human antibodies have been developed which neutralize CTGF or its receptor. The antibodies are drawn from certain transgenic mice bearing human immunoglobulin genes to produce human antibodies. Antibodies that neutralize growth factors or receptor binding have been shown to neutralize effects for periods from 15 days to 1 months.

b) Generation of Active Fragments

The C-terminal fragments have the ability to stimulate cell proliferation, while the N-terminal region stimulates matrix production. Antibodies specific to biologically active fragments of CTGF are far more specific in their antagonistic activities. Because of these specific functions, control of functional regression can be achieved by carefully controlling either or both proliferation or matrix production. In this way, scleral wound healing and healthy cell turnover is promoted without the accompanying stromal remodeling that promotes regression.

c) Small Molecules Inhibiting CTGF Expression

CTGF receptors have been isolated and identified and the signal transduction pathways activated by these receptors have been characterized. Small molecules which block the induction of CTGF have also been identified. It appears that these compounds have the ability to block collagen production in cells exposed to fibrogenic cytokines. They will thus also have the ability to be used to inhibit functional regression, since reduced collagen production will allow the scleral changes induced by tendinoplasty to persist intact without stromal remodeling.

d) Antisense Inhibition of CTGF Pathway

Portions of nucleotide sequence complementary to DNA or RNA sequences encoding CTGF or portions thereof, or CTGF promoter or other regulatory sequences, may be used to prevent induction of CTGF. Methods known in the art to produce and implement antisense therapeutics are within the scope of the invention, and are applicable to inhibit CTGF or any other component of the molecular cascade discussed herein. Antisense therapy directed to any step that inhibits apoptosis, necrosis, fibroblast migration or proliferation, or collagenesis is included in the invention.

(c) Inhibition of Prolyl Hydoxylase

Collagens make up about 30% of the total body proteins. They are the major structural proteins that hold cells together and determine tissue and organ architecture. In fibrotic disorders, collagen molecules are synthesized and secreted in excess, and the resulting fibrotic scar tissue is comprised of a strong cross-linked collagen scaffold. Attention has been focused upon key enzymes required for collagen formation and deposition as a target for inhibition of the formation and accumulation of collagen which leads to fibrotic scar.

Figure 2:
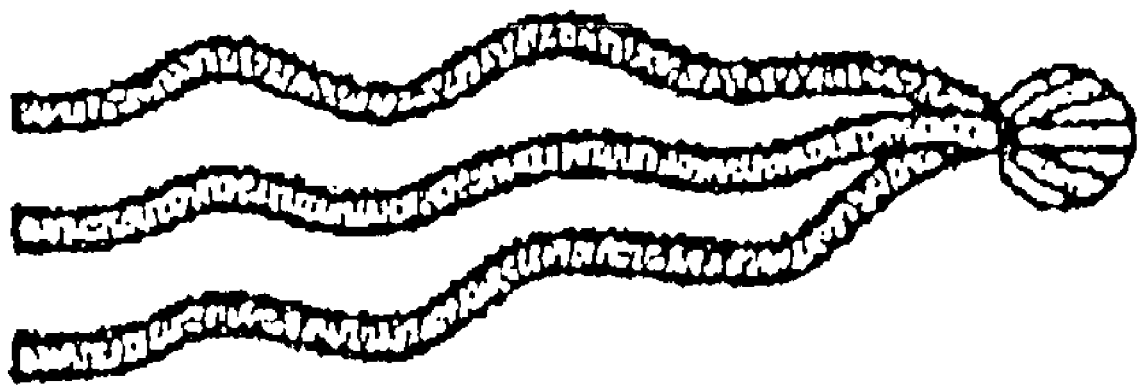
FIG. 2 is a schematic of the formation of hydroxylated procollagen from nonhydroxylated procollagen catalyzed by prolyl hydroxylase.
Figure 2:
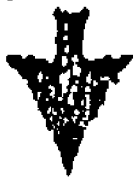
Figure 2:

Prolyl-4-hydroxylase (P4Hase) is an intracellular enzyme required for the synthesis and formation of all the 20 known types of collagen, therefore representing an important target for anti-fibrotic therapies. P4Hase works inside the cell by modifying polypeptide chains to allow them to form stable triple-helical structures. Prolyl hydroxylase catalyzes the hydroxylation of prolyl residues to 4-hydroxyproline during post-translational modification of collagen. The formation of hydroxyproline enables the molecule to form the stable triple helical conformation typical of collagen (FIG. 2).

Hundreds of thousands of compounds have been screened in high throughput screening (HTS) for assaying diverse organic compounds against this target. A recombinant expression system has been established to produce large quantities of prolyl hydroxylase. Effective inhibition of the activities of this enzyme prevents the assembly of all types of collagen. Novel compounds that inhibit prolyl hydroxylase have been identified, and these have been tested in secondary screens to determine efficacy, toxicity and potency. Additional compounds have been developed from promising leads by focused combinational chemistry.

Selected compounds have been tested for oral and topical administration, and the compounds have been found to be active and effective in both forms. Safety has been demonstrated in 14-week administration. In these pre-clinical tests, functional improvement was also demonstrated.

Collagen synthesis has been blocked using a novel inhibitor identified as FG-041 in an animal model. Scar formation has been prevented and wound healing and tissue regeneration has been improved. The effect is maintained on withdrawal of the drug after local administration. In other studies, the drug was well tolerated and showed good pharmacodynamics after oral drug delivery. Another compound, FG-1648, a water-soluble inhibitor of prolyl hydroxylase, has been shown to be effective by means of topical administration in a pig model for dermal wound scarring. The safety and efficacy of these compounds make them promising therapeutics for topical ophthalmic administration for use in regression therapy. Their short term use would inhibit regression via stromal remodeling, but would avoid the side effects of long-term suppression of collagen formation that could impair scleral health.

The regression of functional effect observed in laser ciliary muscle tendinoplasty is the result of the trauma-induced wound repair cascade. Collagenesis is the culmination of this event. Thus, ophthalmic administration of compounds inhibiting the prolyl hydroxylase required for collagen biosynthesis and assembly would prevent or control the functional regression.

(d) Inhibition of C-Proteinase

Figure 3:
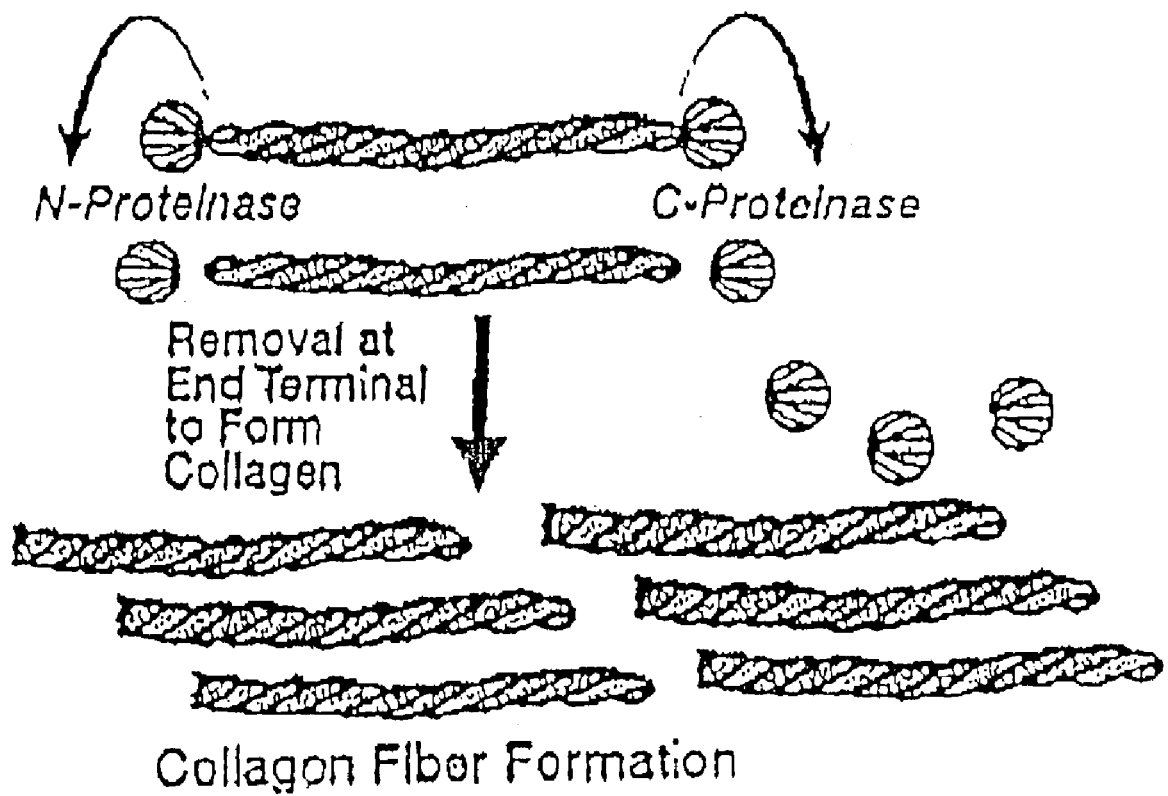
FIG. 3 is a schematic of the formation of collagen fibers following the cleavage of the C and N terminals of the procollagen molecule by C-Proteinase and N-Proteinase, respectively.

After procollagen is secreted from the fibroblast, C-proteinase is the enzyme that then coverts the procollagen into collagen, a necessary step in the formation of types I, II, and III collagen by removing the carboxy terminal domain of the procollagen (FIG. 3).

U.S. Pat. No. 6,020,193 to Prockop (herein incorporated by reference) teaches purified C-proteinase and sufficient amino acid sequence to identify, clone and express this protein. C-Proteinase is an important target for inhibition in tendinoplasty regression due to its selective effects on formation of types I and III collagens. It converts fibrillar collagens to collagen by removing the carboxyl terminal globular domain, thereby enabling assembly into larger collagen fibrils. By blocking the action of C-proteinase, procollagens can not assemble into collagen fibrils. As a consequence, C-proteinase inhibitors can block the proliferative effects of types I and II collagen that induce functional regression, without affecting the formation of other types of collagen.

Three alternative forms of C-proteinase have been identified, including bone morphogenic protein, or BMP-1, M-tolloid and M-tolloid-like protein (see, e.g., U.S. Pat. No. 5,939,321). Two methods have been created for the blocking of these enzymes, monoclonal antibodies and small molecule compounds. It is understood for this and all other antibody therapeutics discussed herein, that polyclonal antibodies or active fragments (e.g., FAb) may be used.

These therapeutic antibodies offer a significant advantage in that they can be directed to the key enzymes allowing the development of therapeutics for specific local, topical and systemic uses. Alternatively, compounds have been and can be identified with high throughput screening processes as anti-regression therapeutics.

Inhibitors identified to date have shown good selectivity in blocking the C-proteinase at 200 to 1000 fold lower levels than matrix metalloproteinases MMP-1, 9 and 13. The development of an animal model for wound healing following laser ciliary muscle tendinoplasty has shown that matrix metalloproteinase-9 (MMP-9) is found in damaged sclera undergoing wound healing. It presents an all-or-none marker since it is not found in the normal cornea, but correlates with the magnitude of laser trauma and resolves in 48 hours. C-Proteinase inhibition should correlate well with the disappearance of MMP-9 in the ophthalmic model and thus provides a sensitive method of monitoring intervention during anti-regression therapy.

(e) Alternative Therapeutics

The methods of the invention can also make use of the following drugs as alternatives for the prevention of refractive regression:

1. Interferon-α
2. 3 hydroxypyridine-2-carboxamidoesters
3. tolloid-like gene product (mTll) and its cognate gene
4. hydroxypyridone compounds
5. 3,4 dihydroxybenzoic acid
6. 3,4 dihydroxyphenylacetic acid
7. p 1894B of Okazaki
8. pyridine-3-carboxylic acids and esters containing a substituted or unsubstituted 5-tetrazolyl group in a 6 position of the pyridine ring
9. pantethine
10. 1,2 diamine compounds
11. 3,3 dihalo-2-propenlyamine compounds and their salts
12. 2,4 or 2,5-disubstituted pyridine N-oxide compounds
13. 2,3-dialkyl-5,6-dimethoxy-p-benzoquinone compound
14. 5-hydroxy-I,4-naphthoquinone compounds
15. oxalylamino acid compounds and their physiologically active salts
16. 2-amino,-6-phenyl-4H-pyran-4-one compounds containing an N-morpholino substituent in the 2 position of the pyranone ring
17. calcium channel blockers chosen from nifedipine, hydropyridine, verapamil, cobalt chloride, and biologically acceptable cobalt salts
18. peptide derivatives
19. pyridine-2,4-and-2,5-dicarboxylic acid amides
20. phenanthroline derivatives
21. pyridoxal benzoyl hydrazones or analogs such as 3hydroxyisonicotinaldehyde benzoyl hydrazone and salicylaldehyde benzoyl hydrazone
22. polypeptide including a sequence of at least about 5 amino acids corresponding substantially to an amino acid sequence from within the 33 kD fragment of the A chain of fibronectin, within the G domain of the A chain of laminin, or within the NCl domain of the α2 chain of the type IV collagen.

Properties of compounds useful in this invention and potential targets for inhibiting regression, as well as information regarding their therapeutic use, can be found, for example, in U.S. Pat. Nos. 5,939,321; 6,010,193; 6,037,139; 5,716,633; 5,811,446; 5,626,865; 6,013,628; 6,020,350; 5,789,426; 5,807,981; 5,916,898; 5,863,530; 6,005,009; 4,499,295; 6,965,586; 5,965,585; 5,620,996; 5,981,717; 5,993,845; 5,998,422; 5,408,040; 5,837,258; 5,770,209 and 5,783,187, all herein incorporated by reference, and other sources known to those of skill in the pharmaceutical arts.

3. Remedial Cross-Linking to Restore Lamellar Stability Following Thermal Ciliary Muscle Tendinoplasty A great deal has been written about the regression of the desired refractive effect in refractive keratoplasty. These changes observed as a function of time have been attributed to the wound repair cascade and subsequent epithelial hyperplasia and stromal remodeling. A frequently overlooked adjunctive process involves the destruction of the stabilizing collagen molecular cross-links. The various intra—and intermolecular cross-links impart to collagen its unique structural integrity. While most of the stability of the triple helical conformation comes from heat-labile hydrogen bonding, surgical intervention also results in proteolytic enzymatic destruction of other cross-links, and may be the first step in the catabolism of insoluble collagen in the cornea. The scleral response to ciliary tendinoplasty is analogous to that in the cornea.

A. The Nature of the Structural Integrity of Collagen

Primary Structure:

The essential features of the primary structure of collagen include the presence of glycine as every third residue and the presence of the amino acids hydroxyproline and hydroxylysine. Proline and hydroxyproline together account for approximately one-third of the amino acids present. There is evidence that the collagen molecule is stabilized by one or more disulfide cross-links in addition to hydrogen bonding.

The individual peptide chains of collagen molecules are twisted into a right-handed helix. This helical twist is the result of the presence of large numbers of amino acid residues, proline, and hydroxyproline. Because one side of the five-sided ring structure of these amino acids constitutes one part of the peptide backbone of the molecule, free rotation of the chain cannot occur at these sites and the backbone of these chains are bent at these points. The net result of the presence of these residues is that the chain of amino acids is forced into the helical configuration. However, there is a short sequence of amino acids (15 in the case of type I collagen) at the N-terminal portion of the molecule that do not have glycine as every third residue. This is know as the "telopeptide" region. This region is not helical, can be attacked by ordinary proteolytic enzymes, and is important in cross-linking.

Secondary Structure:

The three peptide chains must be held together in some fashion to make a molecule. When first assembled, the three chains are held together by relatively weak forces. The molecule thus formed, before it has become polymerized into fibrils and fibers, is referred to as "tropocollagen". The term collagen usually refers to the polymeric aggregation of a number of tropocollagen units to form a long polymeric chain. Covalent cross-links can form among the three chains.

Figure 4:
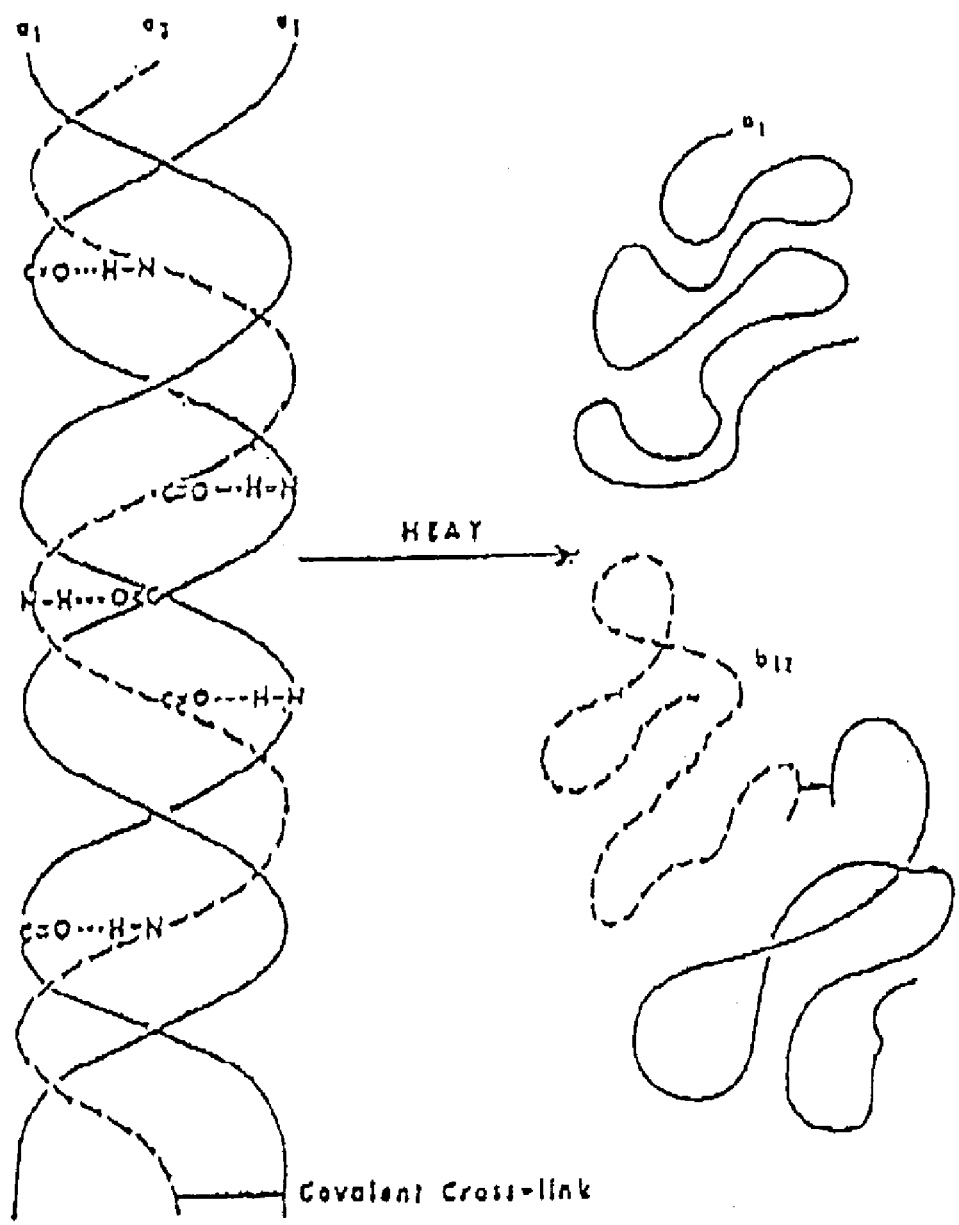
FIG. 4 illustrates the manner in which hydrogen bonds form between $\infty$ chains in the tropocollagen molecule and provide stability to the triple helical structure. Heat above 60° C. will denature collagen and cause the collapse of the helical configuration and the separation of individual chains into random coil configuration. The intramolecular cross link is unaffected and the two chains remain linked in the denatured state.

Tertiary Structure:

The spatial arrangement of three chains in the molecule also is unique to collagen. The a chains are right-handed helices, and the three helices are then twisted into a left-handed "super helix". The entire structure is held together by hydrogen bonds (FIG. 4).

Hydrogen bonds are formed between a hydrogen atom and a strongly electronegative atom such as F, O, or N. In proteins, a hydrogen attached to an amino group or a hydroxyl group may form a bond within adjacent oxygen derived from a carboxyl group. Hydrogen bonds are quite weak and can be broken by mild heat, such as that which is generated by laser thermal or conductive radiofrequency keratoplasty. When this happens, the helical structure of the molecule is destroyed and individual chains separate as randomly coiled structures. In the case of collagen, this gentle heating leads to hydrogen bond rupture and denaturation of the collagen. This process is inherent in the thermal tendinoplasty methods also and results in collagen fibrillar shrinkage or contraction. If the thermal profile is uncontrolled and exceeds the thermal shrinkage temperature of collagen (Ts), collagen is reduced to parent gelatin and loses all structural integrity.

Figure 5:
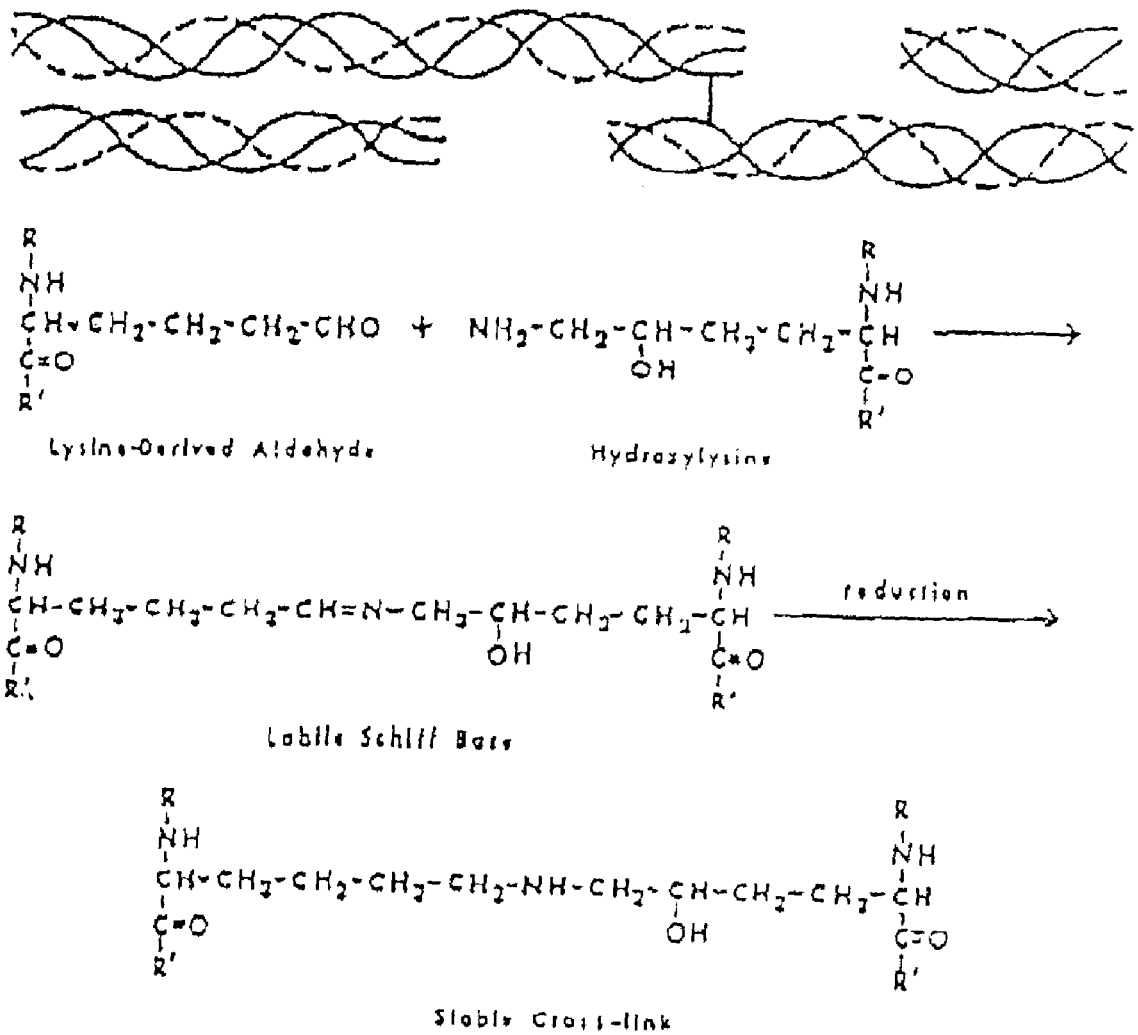
FIG. 5 shows the intermolecular cross-linking between collagen molecules. At the top, the cross-link is shown as bonding a lysine in the amino terminal of a tropocollagen molecule with a hydroxylysine near the carboxyl terminal of another tropocollagen molecule. In the lower part of the Figure are the proposed reactions leading to stable intermolecular cross-links.

Quaternary Structure:

The quaternary structure of collagen, or the way tropocollagen is aggregated into a stable biological unit of great mechanical strength, is important to the mechanical properties of collagen (FIG. 5).

In the course of aggregation and during cross-linking, the solubility of collagen undergoes change. Collagen is no longer soluble in water when so aggregated but can be solubilized in neutral salt solutions. Initially, the forces holding chains of tropocollagen together are electrostatic. Salt serves to neutralize the electrostatic forces holding the molecules together and thus solubilizes collagen. As intermolecular cross-links form, collagen losses its salt solubility, but can be solubilized in dilute acid, such as 0.5 M acetic acid. The major intermolecular covalent cross-links that form are aldimines which hydrolyze in acid solution. As these aldimine bonds become reduced or substitutions occur across the double bond, collagen fibrils become completely insoluble, even in acid.

A model of the collagen fibril, based upon physical chemistry, describes the microfibril of collagen as held together by covalent cross-links and the bundles of micro fibrils are "cemented" together to form fibrils by protein polysaccharide of glycoproteins.

As a fibril grows, each succeeding chain is distorted or twisted a bit more because of increasing surface of the fibril. This introduces a stress into the polymer and it requires force to maintain this stressed position. This force is provided by ionic or charge attraction between bonding sites in the tropocollagen chain.

Collagen Maturation:

Maturation of collagen can be defined as the process by which the fragile, soluble fibers of collagen change into strong, insoluble fibers and how they proceed from a disorganized, random, and not very useful arrangement to an oriented, organized structure providing mechanical strength to a tissue.

One of the most stable cross-links arises from a shift of the double bonds to yield a ketone. Thus, these bonds and others such as more complex rearrangements involving other amino acid side chains, including the imidazole group of histadine, are the major force holding fibrils and fiber bundles together. Their presence is the chief contributing factor in the tensile strength of collagen.

It is important that for intermolecular bonds to form, the participating groups must be packed closely together. There is evidence that mechanical tension may play a role in packing the chains so that these cross-linking reactions are facilitated. The formation of an intramolecular bond does not alter the solubility of collagen, but it does make the molecule much more resistant to attack by enzymes. There is also evidence of covalent linkage fibrils to the glycoproteins of the stromal ground substance.

Covalent cross-linking is important in the maturation of collagen and in the tensile strength of wounds. The introduction of cross-links by local treatment of a healing wound with cross-linking agents should hasten the increase in tensile strength. This has, in fact, been the case in controlled studies. The thermal shrinkage temperature of the individual collagen fiber was increased in treated wounds as compared to fibers from comparable control wounds.

Disclosed herein is the administration of cross-linking agents by topical ophthalmic delivery to a thermally damaged sclera to enhance the structural recovery of the tissue. We have applied this concept to laser and radio frequency conductive ciliary muscle tendinoplasty.

B. Causes of Lamellar Structural Instability

One of the great paradoxes in refractive keratoplasty is demonstrated in laser thermal keratoplasty. LTK requires heat to reduce the hydrogen bonds in order to obtain efficacious cornea shape change by means of collagen fibrillar shrinkage. Hydrogen bonds are quite weak and can be broken by mild heating. When this happens, the helical structure of the molecule is destroyed and individual chains separate as randomly coiled structures. In the case of collagen, mild heating, which leads to hydrogen bond rupture, produces denaturation; parent gelatin is the resulting product. The absence of the triple-helical formation of the molecule leads to extreme fragility of the structural integrity.

When collagen is denatured from exposure to elevated temperature and its tertiary structure destroyed, it is quite susceptible to attack by trypsin, pepsin and other proteases. This increases its heat-lability and lowers thermal shrinking temperature of the collagen, thus reducing its tensile strength even more. It may also lead to the secondary destruction of other collagen stabilizing cross-links. This, then, forms the basis for lamellar instability and regression of desired functional result following laser thermal tendinoplasty and other modalities which rely upon heat to induce collagen shrinkage for functional modification.

The hydrothermal shrinkage of the collagen molecule occurs within a small temperature range, from 60 to 70° C., and is attributed to the cleaving of the internal stabilizing cross-links. Exceeding this temperature range will further damage these cross-links and culminate in scleral lamellar instability.

Early relaxation (leading to refractive regression) of the tension exerted by the hydro-thermal shrinkage of collagen fibers will depend upon the nature of the inherent cross-links in the collagen network. Hydrolysis of the heat-labile cross-links has been shown to be one of the causes. Two phenomena will compete during the hydrolysis of these heat-labile bonds: relaxation following the decrease in the number of meshes and eventually the larger diameter of the remaining ones, and the rise in tension induced by the temperature effects on the resistant network. The parameters influenced by the hydrolytic reaction of the network nodes are time and temperature, as well as "stress" dependence. Other parameters depend upon cross-link density and the presence of the heat-stable cross-links that are responsible for the residual tension.

The fibroblast, or keratocyte in the case of the cornea, is the cell primarily responsible for the synthesis of collagen. When a wound occurs, the fibroblast is among the first cells to appear. Amino acids are picked up by specific transfer RNAs and incorporated into growing peptide chains within these cells and become collagen precursors or procollagen.

Collagen chains exist as a helical coil arranged parallel to each other. The alpha chains are right-handed helices, and three helices are then twisted into a left-handed "superhelix". This entire structure is held-together by hydrogen bonds. Hydrogen bonds (FIG. 4) are formed between a hydrogen atom and a strongly electro-negative atom. In proteins, a hydrogen attached to an amino group or a hydroxyl group may form a bond with an adjacent oxygen derived from a carboxyl group. Hydrogen bonds are quite weak and can be broken by mild heat. When this happens, the helical structure of the molecule unwinds and the collagen molecule contracts.

If covalent cross-linking is important in the maturation of collagen and in the tensile strength of wounds, the introduction of cross-linking by local treatment of a healing wound with cross-linking agents would be expected to hasten the increase in tensile strength. This experiment has been performed with formaldehyde in one instance and 1-ethyl-1-3 (3-dimethylaminopropyl) carbodiimide hydrochloride in another. It was suggested that formaldehyde would introduce methylene bridges between adjacent tropocollagen chains. The carbodiimides have been shown to be useful in forming amide bonds during protein synthesis. With both agents there was a sizable increase in tensile strength of the wounds as compared with controls. The thermal shrinkage temperature of the individual collagen fibers from the wounds was increased in treated wounds as compared to fibers from comparable controls. These facts suggest that cross-linking after fibril formation is an extremely important aspect responsible for the mechanical properties of collagen, particularly tensile strength.

The greatest bulk of scleral stroma consists of collagen fibers of uniform diameter gathered into bundles or scleral lamellae. Each successive lamellar layer has collagen fibrils, which pass to the ones above and below it. Each fiber is embedded in a characteristic matrix, or ground substance. The possible stabilization of collagen fibrils through covalent bonding with glycoprotein to collagen also plays a role in the physical properties of the collagen fibril and may regulate the size attained by the fibril.

Figure 6:
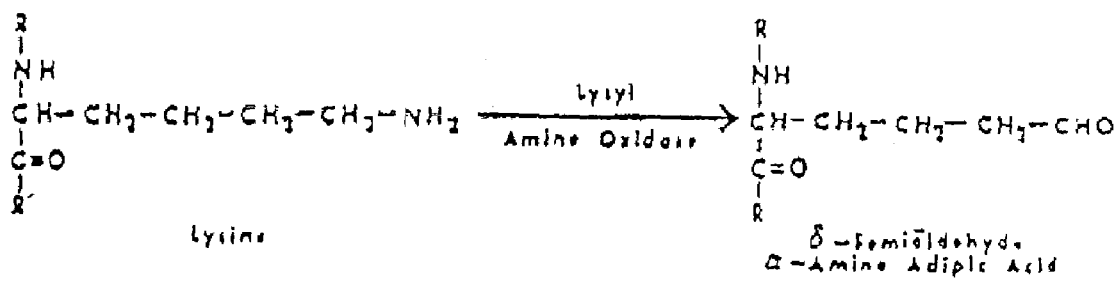
FIG. 6 shows intramolecular cross-linking. At the top is shown amino acid sequences of the amino ends of the three peptide chains of the tropocollagen molecule. A cross-link between lysines in an $\infty 1$ and the $\infty 2$ chain is shown. Postulated steps in the formation of this cross-link are shown in the lower Figure.
Figure 6:
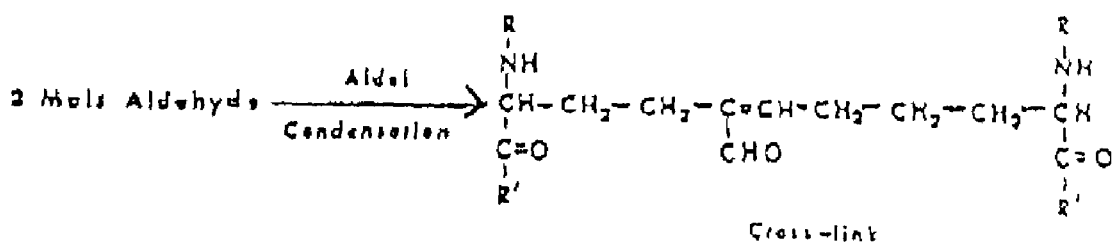

All of the physical properties of collagen, such as the tensile strength, are affected by cross-linking. The lamellar instability which results from thermal tendinoplasty, whether by coherent, radiofrequency radiation or any other method of thermally modifying the scleral collagen matrices, is directly related to rupture of the collagen intermolecular hydrogen bonds which are heat labile. The heat generated by thermally mediated corneal processes may also alter certain intramolecular cross-links (FIGS. 5 and 6).

Regressive modification of the desired scleral change following thermal tendinoplasty is directly related to these biochemical alterations. The introduction of cross-linking agents at the time of, or subsequent to, thermal injury would hasten the increase in tensile strength of the sclera and would provide stability to the resultant functional modification.

C. Methods and Devices for Restoration of Lamellar Stability

Incomplete cross-linking of tissues and the structural collagenous network can lead to enhanced biodegradation, antigenicity and loss of mechanical function. Prior art cross-linking techniques have made use of homo- and heterobifunctional reagents, both of which form chemical cross-links by introducing bridges between amino acid chains. Limitations of some cross-linkers have been obviated by the use of rapidly cross-linking photosensitive agents. Upon photoactivation by the use of ultraviolet or visible irradiation, the photoactivatable site is converted to a species of very high chemical reactivity which forms a covalent linkage with another amino acid side chain. The absorption of the UV or visible radiation by the bifunctional reagent can give rise to two general classes of species produced by the cleavage of chemical bonds.

Two methods exist for the photoactivation of heterobifunctional compounds. One is accomplished by means of irradiation with a short wave UV lamp. The half-time of photolysis is in the order of 10 to 50 seconds depending upon the reagents used. The other method is flash photolysis for an extremely short period on the order of milliseconds.

In past investigations, chemical agents, in particular glutaraldehyde, were found to have application for the biosynthesis of intramolecular and intermolecular cross-links. This process has been used commercially in vitro to stabilize pig heart valves used in valvular replacements. Other applications have been in the development of tissue bioadhesives for sutureless closures of wounds and in the development of contact lens material, lens or corneal implant material, a wet occlusive bandage, patch graft, implant material to replace silicone in cosmetic plastic surgery, artificial joint lining material and as a drug delivery mechanism.

In each case, all of the applications of this process for cross-linking any amino acid-containing polymer have been in vitro. The introduction, in vivo, of collagen cross-linking agents during or immediately following thermal modification of the sclera for ciliary muscle tendinoplasty is proposed for enhancing the lamellar structural integrity thus weakened by the thermal keratoplasty. This will prevent the transient stress-induced regression normally observed.

One such method and apparatus is the utilization of spray or drop instillation. A biodegradable collagen shield saturated with this photosensitive agent can also be utilized followed by photoactivation by short-wave UV or visible photonic radiation. Unique to this method is the fact that while one end of the bifunctional reagent forms peptide-like bonds with the collagen amino acid side chains, the other end remains unbound until photoactivation. This end is then converted to a highly reactive compound called a "nitrene" or a "carbene", which in turn bonds with an amino acid side chain of tissue collagen.

The concentration of the cross-linking reagent mixtures used in this application may vary between 5 µM and 250 mM dissolved in a biologically compatible solvent such as, but not limited to, DMSO.

Photoactivation of the reagents can be achieved within a wave length range of 220 nanometers to 310 nanometers. The duration of the photoactivation will vary depending upon the cross-linker used.

An additional cross-linking system is presented which utilizes the vitamin B2 or riboflavin as the photomediator. It can be instilled in several ways to be outlined. Once the cornea is so treated, the stained cornea is irradiated or exposed to a 400 nm ultraviolet light source for about 30 minutes. This photoactivation yields $O_2$ which creates new cross-links between the collagen fibers. The corneal structure has been shown to be stiffened by a factor of approximately 1.6 using this method.

Photoactivation, depending on the wavelength and time required, may cause additional epithelial trauma. It may, therefore, be preferable to utilize cross-linking agents, which do not require photoactivation. Broad classes of cross-linking reagents, in addition to those requiring photoactivation, are included in this invention for the purpose of re-establishing the structural integrity of the corneal lamellae. Among these classes are those reagents that use additional non-toxic chemicals or heat to complete the desired chemical reaction.

A preferred cross-linker of the invention is glycerine or glycerol. Glycerol is the simplest trihydric alcohol, with the formula $CH_2OHCHOHCH_2OH$. The name glycerol is preferred for the pure chemical, but the commercial product is usually called glycerin. It is widely distributed in nature in the form of its esters, called glycerides. The glycerides are the principal constituents of the class of natural products known as fats and oils. It is completely soluble in water and alcohol and has a very low toxicity in mammals. It has properties that allow it to stabilize lamellar structures without the need to photo activate it. Because it requires no potentially damaging photoactivation, has very low toxicity, and is a common additive to food items, it provides the advantage of an effective, non-toxic, inexpensive cross-linking reagent that is very suitable for human use.

4. Pharmacokinetics

A. Factors Influencing Drug Penetration into the Sclera

While there are several factors that differentiate the use of anti-fibrotic and cross-linking therapy in the sclera from other tissues in the body, pharmokinetics is of prime importance. Drug absorption into the sclera presents unique challenges.

The anti-fibrotic and cross-linking drugs and reagents can be instilled in several different ways but these agents must penetrate the physical barrier that the sclera presents. Drugs appear to penetrate the sclera by diffusion and the rate of diffusion parallels the drug concentration. The epithelium is the first barrier and drugs must enter this layer rapidly or be washed away. Cell membrane lipids, which are present within the five layers of the epithelium, limit drug penetration. The epithelium contains hydrophilic constituents, which also retard drug penetration.

For there to be clinical significance in the restoration of stromal lamellar stability by means of reagents or drugs, the drugs must be presented to the cornea in a 'bioavailable' manner. The bioavailability of a drug product is defined as the percentage of the reagent that is absorbed. In addition to bioavailability, the other important parameter to be considered is the pharmokinetics of the drug in the patient's tissues. Many factors will alter each parameter and will result in the choice of method or means of administration of the reagent of choice.

Among the pertinent factors are the excipients or inactive compounds present in the drug such as diluents, lubricants, binders and the like, which are important determinants of bioavailability. Variations in dissolution rate are also important. The pH of the drug solution determines whether it is the ionized or non-ionized form. The non-ionized form, being more lipid soluble, is better able to penetrate the scleral epithelium. Viscosity will affect the drug-contact and, therefore, its bioavailability. Surfactants or detergents may be used to increase the solubility of drugs that are hydrophobic. Osmotics may be added to adjust the tonicity of the ophthalmic solutions to that of the tears.

Lacrimal volume will affect the concentration of the drug, but reflex tearing can be minimized by the prior administration of a local anesthetic and drug absorption can be increased by altering the epithelium. Eye drop size and/or punctal occlusion will result in greater reagent concentration being available.

B. Modes of Drug Delivery

The reagents or drugs are presented to the sclera by one of three modes of administration:

(1) Topical administration of solutions, suspensions, ointments, powders, particulates, and the like, by periodic or continuous irrigation (FIGS. 7a and 7b), and aerosol spraying (FIG. 7c), iontophoresis, or the like.

(2) Applications of drug reservoirs, such as pledgets (usually, squares of pressed cotton), or sponges soaked with a drug (FIGS. 8b and 8c), soft contact lenses soaked in a reagent (FIG. 8a), polymer drug delivery systems, collagen shields soaked in the drug (FIG. 8a), liposomes, flexible capsules or wafers, or other membrane or reservoir systems (FIG. 8d), and (3) Subconjunctival injection (FIG. 9).

Solutions and aqueous suspensions are the pharmaceutical forms most widely used to administer drugs that must be active on the eye surface or in the eye after passage through the conjunctiva. To increase bioavailability of drugs, to extend therapeutic efficacy, and to improve patient compliance, various dosage forms have been developed over the years. These include soluble inserts (undergoing gradual dissolution/or surface erosion), insoluble inserts (e.g., medicated contact lenses such as Ocusert™, etc.), gels (e.g., Gelrite™), liposomal and drug delivery via nanoparticles (emulsion, suspension, etc.), and ointment (See Edman, Biopharmaceutics of Ocular Drug Delivery, CRC Press, 1993). Suspensions require shaking well before administration to ensure the particles are well dispersed in the suspension solution.

Figure 7A:
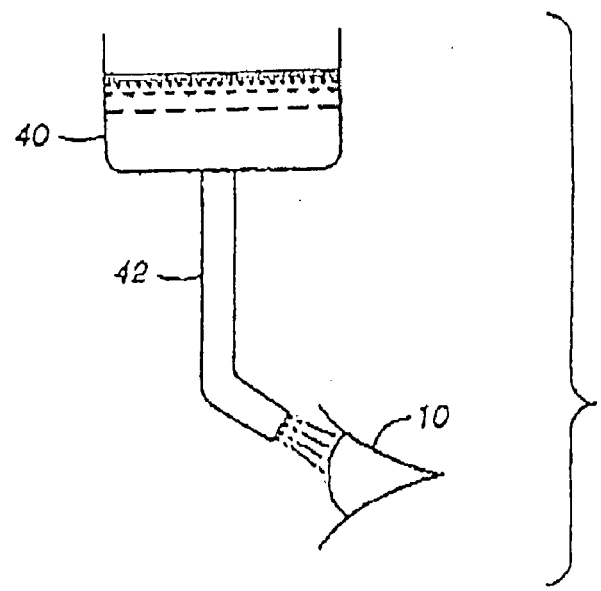
FIGS. 7a–7c show various methods of instilling therapeutics into the eye, such as by irrigation (7a), periodic irrigation via drops (7b), and aerosol spraying (7c).
Figure 7B:
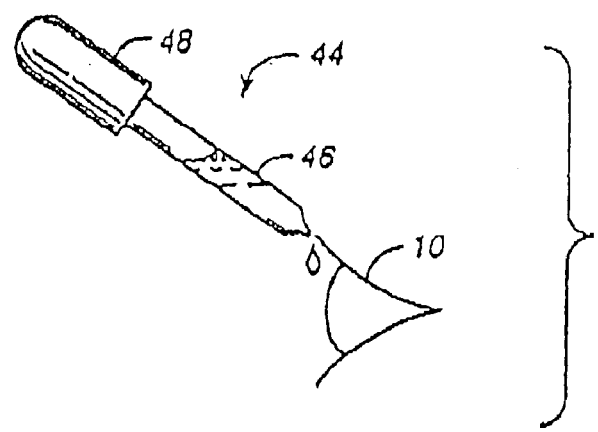

The combinations of powders and periodic irrigation, such as by eyedropper 44 in FIG. 7b, or continuous irrigation, such as by reagent reservoir 40 and irrigation tube 42 in FIG. 7a, may be useful. As shown in FIG. 7b, periodic irrigation may be achieved by the use of eyedropper 44, having reagent reservoir 46, and pressure bulb 48, to deliver reagent to the eye 10.

Alternatively, such periodic irrigation can be achieved by similar periodic drip systems, either manual or automated. As shown in FIG. 7a, continuous irrigation may be achieved by use of reagent reservoir 40 which feeds reagent, either by gravity or controlled feeding, to irrigation tube 42, and thereby to the eye 10. Alternatively, such continuous irrigation can be achieved by similar continuous reagent supply systems, either manual or automated.

Figure 7C:
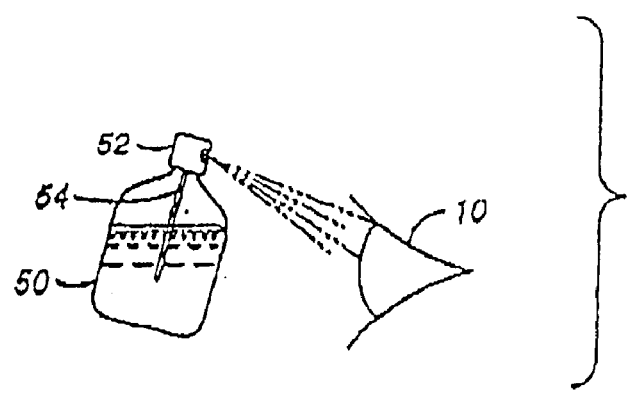

Similarly, aerosols may be employed, such as by use of a reagent reservoir 50 and aerosol device 52, including reagent access tube 54, of FIG. 7c. Periodic or continuous irrigation, or aerosol spraying, should be used to irrigate, or to spray the eye, respectively, with reagent for about five minutes or until the reagent has sufficiently penetrated the corneal epithelium. When periodic irrigation systems, continuous irrigation systems, or aerosol devices are used, the reagent should be applied before the blink reflex. Alternatively, means can be employed to inhibit the blink reflex and, thus, facilitate the delivery of reagent by any of these systems.

Iontophoresis is largely of historical significance to aid the penetration of ionizable drugs having limited lipid solubility. This technique works by placing one electrode upon the cornea usually embedded within a scleral contact lens in the presence of a drug solution. The other electrode can be placed anywhere else on the body. In iontophoresis, the electrode, the current, the topical anesthetic, the hypertonic solution, and the non-physiologic pH-aided drug penetration may cause some corneal epithelial damage. If the epithelium is breached, the current alters the steady state of the stroma and, therefore, the Ts (thermal shrinking temperature), thus adding another variable that may pertubate the results.

In administration by subconjunctival injection, a syringe 64 of FIG. 7 is used to penetrate the subconjunctiva, the "mucous membrane" of the eye which lines the inner surface of the eyelids and is reflected over the fore part of the sclera and the cornea, and to deliver a reagent to the subconjunctival tissue. Syringe 64 includes needle 66, typically a 25 gauge, reagent reservoir 68, and plunger 70 (shown in part) in FIG. 9. In use, the needle 66 is placed adjacent the conjunctiva, as schematically illustrated by the dashed line of FIG. 9, pressed against the conjunctiva to penetrate into the subconjunctival tissue, and plunger 70 is pressed to deliver reagent from the reagent reservoir 68 to the subconjunctival tissue. The injection is usually directed to the perilimbal portion of the subconjunctiva.

Certain aspects of the injection of the reagent, such as patient apprehension, subsequent inflammatory response, pain, inconvenience, and expense should be evaluated against the advantageous aspects of this method.

Pledgets 58 of FIG. 8b or sponges 60 of FIG. 8c, usually smaller than a contact lens 56 of FIG. 8a, are soaked (as indicated by a droplet) with a reagent and then placed inside one or both lids, adjacent the cornea 11 of FIG. 8a, for about five minutes or until the reagent sufficiently penetrates the cornea 11. Pledger 58 may be composed of a fibrous material, such as cotton or cellulose, as illustrated by the curved and overlapping lines in the interior of pledger 58 of FIG. 8b. Sponge 60 may be composed of known sponge materials, such as cellulose, its sponge-like characteristics being illustrated by the void, and non-void spaces in the interior of the sponge 60 of FIG. 8c. While pledger 58 is often a cotton square, when placed adjacent the cornea 11 in the same manner as described below with respect to the contact lens 56 of FIG. 8a, it substantially conforms to the shape of the cornea 11. Similarly, sponge 60 substantially conforms to the shape of the cornea 11 when it is placed adjacent the cornea 11 in the same manner. For simplicity, pledget 58 and sponge 60 are shown in two dimensions, it being understood that pledger 58 and sponge 60 have substantially the three-dimension configuration of a contact lens 56 of FIG. 8a.

While the above described delivery systems are quite effective, drugs contained within a membrane device 62 of FIG. 8d and placed within the conjunctival sac produce a more even release of drug than any topical system. Membrane device 62 is left in the conjunctival sac for about five minutes or until the drug or reagent sufficiently penetrates the cornea 11. These membrane devices 62 may take the form of flexible capsules, shaped as semi-circular wafers, which are placed in one or both eyelids (usually the lower eyelid), although other forms are contemplated. While the lipophilic or hydrophilic nature of the membrane, the pore size, and the membrane thickness may mitigate the rate of drug release, such membrane system may have advantages over other modalities. For example, excipients can be avoided, tear pH is not acutely lowered and lacrimal washout is not a factor.

Liposomes, which are synthetic phospholipid vesicles, absorb to the corneal epithelium cell membrane and transfer drug directly. Liposomes are generally described in published international patent application under the Patent Cooperation Treaty, International Publication No. WO 86/03938, of inventors John H. Crowe and Lois M. Crowe (International Filing Date of Jan. 8, 1986), on pages 1 and 2. The entire disclosure of these pages is incorporated herein by this reference. The primary limitations of liposomes are their limited binding power to the epithelium and their expense.

Hydrophilic soft contact lenses 56 of FIG. 8a have been used as drug reservoirs with success. Polymer drug delivery systems, while effective, are generally more rigid than soft contact lenses 56. Particularly preferred are cross-linked collagen shields 56, also shown of FIG. 8a, which are shaped like contact lenses 56 and are used to both promote corneal epithelial healing and to provide drug delivery. Because they conform to the shape of the cornea 11, multiple base curves are not required. They are also biodegradable and thus provide protection to the cornea during the post-laser recovery period after the drug is dissipated and do not require removal.

As schematically shown in FIG. 8a, a pre-soaked (as indicated by a droplet) contact lens 56 or collagen shield 56 which is shaped to conform substantially to the cornea 11 is placed (as indicated by the pair of parallel direction arrows) in contact with the cornea 11 of an eye 10 of a patient. As further explained herein, the patient's eyelids are closed over the shield for about five minutes or until the reagent sufficiently penetrates the cornea 11.

The ideal system combines the administration of topical anesthetic, such as proparacaine, with the efficient administration of reagent by means of a collagen shield. Topical anesthetic is used to breach the epithelial barrier and to provide, simultaneously, desensitization for the laser exposure. Presenting topical anesthesia by this method provides protracted desensitization for comfort following the laser exposure and, by way of the collagen shield, protects the surface epithelium preventing denudation. The reagent further provides the intermolecular stabilization necessary of the corneal stroma following the destabilizing laser treatment.

These and other possible ophthalmic drug administration devices and methods (including mucoadhesive polymers, particulates, liposomes, ocular iontophoresis, ocular films, ocular inserts and corneal collagen shields), are described in A. K. Mitra, *Ophthalmic Drug Delivery Systems*, 58 Drugs and the Pharmaceutical Sciences Series (February 1993). Fundamentals and applications of controlled drug delivery systems are further provided in J. R. Robinson and V. H. L. Lee, *Controlled Drug Delivery*, 29 Drugs and the Pharmaceutical Sciences Series (2nd Edition).

The corneal collagen shield is an ophthalmologic product available from such companies as Chiron and Bausch & Lomb. The shield resembles a translucent contact lens and is fabricated from bovine or porcine collagen tissue, which resembles the collagen molecule of the human eye.

All of the drug reservoir systems and devices are effective in presenting adequate reagent to the stroma for inhibition of stromal remodeling and in the restoration of lamellar stability process.

at least one selected location sufficient to induce hydrothermal collagen fibrillar shrinkage leading to a refractive change; and cooling the scleral epithelium at least one of prior to, concurrent with, or subsequent to, the application of the thermal energy, so that heat generated by the thermal energy to the sclera that radiates through the epithelium is unable to cause epithelial thermal trauma in at least some epithelial cells through which the energy is transmitted, so that fewer epithelial cells apoptose than would without cooling.

2. The method of claim 1 wherein the thermal energy is selected from photothermal coherent energy and radio frequency conductive energy.

3. The method of claim 1 wherein the cooling is achieved by spraying a cryogenic solution on to the scleral surface.

4. The method of claim 1 wherein the cooling is achieved by a cooled contact device placed onto the sclera.

5. The method of claim 4 wherein the contact device is fabricated of a material having thermal mass sufficient to remain cooler than ambient temperature for the duration of the stromal thermal elevation and which transmits about 100% of mid-infrared irradiation.

6. The method of claim 4 wherein the contact device is fabricated of a material comprising at least one of sapphire and quartz.

7. The method of claim 4 wherein the cooling contact device is fabricated with a base radius of curvature flatter than the apical radius of curvature of the sclera upon which it placed.

The invention claimed is:

1. A method of thermal ciliary muscle tendinoplasty which prevents or inhibits a subsequent loss of functional effect caused by thermally induced scleral epithelial apoptosis, the method comprising:

applying thermal energy to the sclera such that the thermal energy increases sub-epithelial stromal temperature in 8. The method of claim 4 wherein the cooling contact device is cooled in place on the sclera by spraying a pharmaceutically acceptable cryogen upon it.

9. The method of claim 8 wherein the cryogen is 1,1,1,2 tetrafluorethane.

10. A method of preventing or inhibiting a loss of functional effect in a patient who is undergoing or has undergone a ciliary muscle tendinoplasty procedure, wherein the loss of effect is caused by stromal-remodeling, the method comprising:

inhibiting at least one step in the stromal remodeling response of the sclera elicited by the thermal procedure by providing an effective amount of a composition that modulates the at least one step, wherein the inhibiting step results in at least one of inhibition of epithelial apoptosis, inhibition fibroblast apoptosis, inhibition of fibroblast necrosis, inhibition of proliferation and migration into the wounded sclera, inhibition of glycosaminoglycan synthesis, inhibition of assembly of collagen, and inhibition of collagenesis.

11. The method of claim 10 wherein the composition inhibits the expression of Connective Tissue Growth Factor or biologically active fragments thereof.

12. The method of claim 10 wherein the composition provided inhibits the accumulation of heat shock protein-70 resulting in an inhibition of collagen assembly to its properly folded state.

13. The method of claim 10 wherein the composition inhibits the effects of Connective Tissue Growth Factor or biologically active fragments thereof.

14. The method of claim 13 wherein the composition comprises an antibody against Connective Tissue Growth Factor or a biologically active fragment thereof.

15. The method of claim 13 wherein the composition interacts with a receptor for Connective Tissue Growth Factor or a biologically active fragment thereof.

16. The method of claim 10 wherein the composition provided inhibits the effects of heat shock protein-70 resulting in an inhibition of collagen assembly to its properly folded state.

17. The method of claim 16 wherein the composition comprises an antibody against heat shock protein-70.

18. The method of claim 10 wherein the composition provided inhibits the effects of C-proteinase in stromal remodeling.

19. The method of claim 18 wherein the composition comprises an antibody against C-proteinase.

20. The method of claim 10 wherein the composition provided inhibits the effects of prolyl hydroxylase.

21. The method of claim 20 wherein the composition comprises FG-1648.

22. The method of claim 20 wherein the composition comprises FG-O41.

23. The method of claim 20 wherein the collagen shrinkage procedure is one of radiofrequency ciliary muscle tendinoplasty and laser thermal ciliary muscle tendinoplasty.

24. A method of preventing or inhibiting a loss of functional effect in a patient who is undergoing or has undergone a ciliary muscle tendinoplasty procedure, the method comprising:

applying an effective amount of a composition that creates or restores cross-links between stromal lamellae, wherein the cross-links increase the stability of the scleral stroma and cause it to hold the shrinkage induced by the ciliary muscle tendinoplasty procedure longer than it would have if the composition had not been applied.

25. The method of claim 24 wherein the composition creates or restores at least one of hydrogen bonds, electrostatic forces, and covalent bonds between lamellar fibers.

26. The method of claim 24 wherein the composition comprises glycerol.

27. The method of claim 24 wherein the composition comprises glucose.

28. The method of claim 24 wherein the composition comprises a photoactivatable substance, and the method further comprises applying photoirradiation to the cornea after application of the composition to activate the composition and create the cross-links.

29. The method of claim 28 wherein the composition comprises riboflavin, and the photoactivation is by ultraviolet light.

30. The method of claim 28 wherein the composition is activated by heat to form cross-links.

* * * * *